(12) United States Patent
Usuda

(10) Patent No.: US 12,029,384 B2
(45) Date of Patent: Jul. 9, 2024

(54) MEDICAL IMAGE PROCESSING APPARATUS, ENDOSCOPE SYSTEM, AND METHOD FOR OPERATING MEDICAL IMAGE PROCESSING APPARATUS

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 624 days.

(21) Appl. No.: 17/167,051

(22) Filed: Feb. 3, 2021

(65) Prior Publication Data

US 2021/0153720 A1 May 27, 2021

Related U.S. Application Data

(63) Continuation of application No. PCT/JP2019/031133, filed on Aug. 7, 2019.

(30) Foreign Application Priority Data

Aug. 17, 2018 (JP) .................................. 2018-153576

(51) Int. Cl.
*A61B 1/00* (2006.01)
*A61B 1/06* (2006.01)

(52) U.S. Cl.
CPC .... *A61B 1/00006* (2013.01); *A61B 1/000094* (2022.02); *A61B 1/00045* (2013.01); *A61B 1/0655* (2022.02); *A61B 1/0661* (2013.01)

(58) Field of Classification Search
None
See application file for complete search history.

(56) References Cited

U.S. PATENT DOCUMENTS 4,556,057 A * 12/1985 Hiruma ................ A61B 5/0071
  600/478
5,749,830 A * 5/1998 Kaneko ................ A61B 1/0638
  348/E5.038

(Continued)

FOREIGN PATENT DOCUMENTS

JP 2006500124 1/2006
JP 2006255021 9/2006

(Continued)

OTHER PUBLICATIONS

"Office Action of Japan Counterpart Application" with English translation thereof, dated Mar. 8, 2022, p. 1-p. 13.

(Continued)

*Primary Examiner* — John P Leubecker
*Assistant Examiner* — Jae Woo
(74) *Attorney, Agent, or Firm* — JCIPRNET

(57) ABSTRACT

A processor device includes an image signal acquiring unit, an image processing unit, and a display control unit. The image signal acquiring unit acquires a digital image signal corresponding to an observation mode from an endoscope. The image processing unit includes a region-of-interest-detection-mode image processing unit. The region-of-interest-detection-mode image processing unit detects a region of interest from an endoscopic image and outputs a detection result of the region of interest and a cumulative detection time period of the region of interest.

18 Claims, 15 Drawing Sheets

(56) References Cited

U.S. PATENT DOCUMENTS

| | | | |
|---|---|---|---|
| 6,395,016 B1* | 5/2002 | Oron | A61B 8/12 |
| | | | 128/898 |
| 9,142,017 B2 | 9/2015 | Serlie | |
| 2002/0161282 A1* | 10/2002 | Fulghum | A61B 5/0071 |
| | | | 600/178 |
| 2006/0122467 A1 | 6/2006 | Harrington et al. | |
| 2008/0207997 A1* | 8/2008 | Higgins | A61B 90/36 |
| | | | 600/114 |
| 2009/0087049 A1* | 4/2009 | Takahashi | G16H 15/00 |
| | | | 382/128 |
| 2009/0137893 A1* | 5/2009 | Seibel | A61B 1/00181 |
| | | | 600/407 |
| 2011/0181709 A1* | 7/2011 | Wright | A61B 1/045 |
| | | | 348/E7.085 |
| 2011/0201993 A1* | 8/2011 | Takei | A61B 1/041 |
| | | | 604/20 |
| 2012/0209123 A1* | 8/2012 | King | A61B 1/0005 |
| | | | 600/476 |
| 2012/0274754 A1 | 11/2012 | Tsuruoka | |
| 2015/0245819 A1* | 9/2015 | Yoshiara | A61B 8/0866 |
| | | | 600/431 |
| 2015/0257635 A1* | 9/2015 | Kubo | A61B 1/00186 |
| | | | 600/109 |
| 2015/0276602 A1 | 10/2015 | Ishihara | |
| 2018/0242817 A1* | 8/2018 | Imaizumi | G06T 11/60 |
| 2018/0247153 A1* | 8/2018 | Ganapati | G06F 18/285 |
| 2018/0249900 A1* | 9/2018 | Imaizumi | G02B 23/2484 |
| 2019/0239718 A1* | 8/2019 | Iwaki | G02B 23/2461 |
| 2020/0058124 A1* | 2/2020 | Iwaki | A61B 1/00045 |
| 2020/0294227 A1* | 9/2020 | Usuda | A61B 1/000094 |
| 2021/0012495 A1* | 1/2021 | Kamon | G06T 7/0012 |
| 2021/0044750 A1* | 2/2021 | Kamon | H04N 23/56 |
| 2021/0058559 A1* | 2/2021 | Tran | H04N 23/55 |
| 2021/0153722 A1* | 5/2021 | Karino | A61B 1/00006 |
| 2022/0354346 A1* | 11/2022 | Kefurt | A61B 1/00006 |

FOREIGN PATENT DOCUMENTS

| | | |
|---|---|---|
| JP | 2011160848 | 8/2011 |
| JP | 2011255006 | 12/2011 |
| JP | 2014502758 | 2/2014 |
| WO | 2014091964 | 6/2014 |
| WO | 2017081976 | 5/2017 |

OTHER PUBLICATIONS

"Office Action of Japan Counterpart Application" with English translation thereof, dated Jun. 14, 2022, p. 1-p. 11.

"International Search Report (Form PCT/ISA/210) of PCT/JP2019/031133," dated Oct. 15, 2019, with English translation thereof, pp. 1-5.

"Written Opinion of the International Searching Authority (Form PCT/ISA/237) of PCT/JP2019/031133," dated Oct. 15, 2019, with English translation thereof, pp. 1-21.

* cited by examiner

MEDICAL IMAGE PROCESSING APPARATUS, ENDOSCOPE SYSTEM, AND METHOD FOR OPERATING MEDICAL IMAGE PROCESSING APPARATUS

CROSS-REFERENCE TO RELATED APPLICATIONS

This application is a Continuation of PCT International Application No. PCT/JP2019/031133 filed on 7 Aug. 2019, which claims priority under 35 U.S.C § 119(a) to Japanese Patent Application No. 2018-153576 filed on 17 Aug. 2018. The above application is hereby expressly incorporated by reference, in its entirety, into the present application.

BACKGROUND OF THE INVENTION

1. Field of the Invention

The present invention relates to a medical image processing apparatus, an endoscope system, and a method for operating the medical image processing apparatus that are for detecting a region of interest such as a lesion portion.

2. Description of the Related Art

In the medical field, image diagnosis is performed for diagnosing a disease of a patient, performing follow-up, or the like by using a medical image such as an endoscopic image, an X-ray image, a computed tomography (CT) image, or a magnetic resonance (MR) image. A medical doctor or the like determines a course of treatment on the basis of such image diagnosis.

In recent years, image diagnosis using medical images has been employing a way of analyzing a medical image and automatically detecting a region of interest to be carefully observed, such as a lesion or a tumor in an organ. In particular, execution of machine learning such as deep learning dramatically increases the accuracy of detecting a region of interest.

JP2011-160848A (corresponding to US2012/274754A1) describes a medical image processing apparatus that performs, in a case where a region of interest such as a lesion portion is detected from a medical image, image processing on the basis of a detection result. In the medical image processing apparatus described in JP2011-160848A, in a case where a region of interest is detected, a time period during which a display style is kept changed is set, and a display image having alert information indicating the region of interest added thereto or superimposed thereon is generated and is kept displayed on a display device until the set time period elapses.

SUMMARY OF THE INVENTION

However, in the medical image processing apparatus described in JP2011-160848A, in a case where a region of interest is detected, alert information is kept displayed until a set time period elapses. In this case, the alert information is kept displayed until the time period elapses even when the region of interest is not present in the medical image any longer. This may cause a situation in which a medical doctor looks for the region of interest that is not present in the medical image during observation, and the alert information may hinder the observation performed by the medical doctor.

An object of the present invention is to provide a medical image processing apparatus, an endoscope system, and a method for operating the medical image processing apparatus that are capable of preventing display based on detection of a region of interest from hindering observation of a medical image.

A medical image processing apparatus of the present invention includes a medical image acquiring unit, a region-of-interest detecting unit, a cumulative detection time period measuring unit, and a display control unit. The medical image acquiring unit acquires a medical image, the medical image being obtained through imaging of an observation target performed by an imaging device. The region-of-interest detecting unit detects a region of interest in the observation target from the medical image acquired by the medical image acquiring unit. The cumulative detection time period measuring unit measures a cumulative detection time period during which the region of interest remains detected. The display control unit causes the region of interest detected from the medical image by the region-of-interest detecting unit to be displayed in a manner of emphasized display and changes the emphasized display in accordance with the cumulative detection time period.

Preferably, the display control unit may maximize an amount of emphasis of the emphasized display at start of detection of the region of interest and gradually decrease the amount of emphasis as the cumulative detection time period increases.

Preferably, in a case where the region-of-interest detecting unit detects a plurality of regions of interest during imaging performed by the imaging device, the cumulative detection time period measuring unit may measure cumulative detection time periods of the respective regions of interest that have been detected, and the display control unit may change the emphasized display in accordance with the cumulative detection time periods of the respective regions of interest.

Preferably, the medical image processing apparatus may include a region-of-interest storage unit that stores cumulative detection time periods of respective regions of interest previously detected by the region-of-interest detecting unit and feature quantity information indicating feature quantities of the respective regions of interest in association with each other; and an identical-region-of-interest determining unit that determines, based on a similarity between any one of the feature quantities of the respective regions of interest stored in the region-of-interest storage unit and a feature quantity of a region of interest newly detected by the region-of-interest detecting unit, whether or not the newly detected region of interest is identical to any one of the previously detected regions of interest. In a case where the identical-region-of-interest determining unit determines that the newly detected region of interest is identical to any one of the previously detected regions of interest during imaging performed by the imaging device, the cumulative detection time period measuring unit may take over and measure the cumulative detection time period of the previously detected region of interest that has been determined to be identical to the newly detected region of interest, and in a case where the identical-region-of-interest determining unit determines that the newly detected region of interest is not identical to any of the previously detected regions of interest, the cumulative detection time period measuring unit may reset and start measuring a cumulative detection time period of the region of interest newly detected by the region-of-interest detecting unit.

Preferably, the region-of-interest storage unit may store latest detection times of the respective previously detected regions of interest in association with the cumulative detection time periods and the feature quantity information. In a case where the identical-region-of-interest determining unit determines that the newly detected region of interest is identical to any one of the previously detected regions of interest during imaging performed by the imaging device and a time interval between the latest detection time of the previously detected region of interest that has been determined to be identical to the newly detected region of interest and a detection time of the newly detected region of interest is greater than a predetermined value, the cumulative detection time period measuring unit may reset and start measuring a cumulative detection time period of the region of interest newly detected by the region-of-interest detecting unit.

Preferably, the medical image processing apparatus may include a treatment recognizing unit that recognizes that a specific treatment has been performed in the observation target. In a case where the treatment recognizing unit recognizes that the specific treatment has been performed during imaging performed by the imaging device, the cumulative detection time period measuring unit may reset and start measuring a cumulative detection time period of a region of interest newly detected by the region-of-interest detecting unit.

Preferably, the display control unit may superimpose, for the emphasized display, a figure on a position of the region of interest in the medical image. Preferably, the display control unit may change, in accordance with the cumulative detection time period, a color of the figure to be displayed for the emphasized display. Preferably, the display control unit may change, in accordance with the cumulative detection time period, a transparency of the figure to be superimposed on the region of interest.

Preferably, the display control unit may change, in accordance with the cumulative detection time period, a shape of the figure to be displayed for the emphasized display. Preferably, the display control unit may cause a frame-shaped figure surrounding the region of interest to be displayed for the emphasized display and change a thickness of a frame of the figure in accordance with the cumulative detection time period.

Preferably, the display control unit may perform the emphasized display by changing a color of the region of interest and return the color of the region of interest to a color before change in accordance with the cumulative detection time period.

An endoscope system of the present invention includes a light source device, an endoscope, a medical image acquiring unit, a cumulative detection time period measuring unit, a display control unit, and a display device. The light source device emits illumination light for illuminating an observation target. The endoscope has an imaging device that performs imaging of the observation target illuminated with the illumination light. The medical image acquiring unit acquires a medical image, the medical image being obtained through imaging of the observation target performed by the imaging device. The region-of-interest detecting unit detects a region of interest in the observation target from the medical image acquired by the medical image acquiring unit. The cumulative detection time period measuring unit measures a cumulative detection time period during which the region of interest remains detected. The display control unit causes the region of interest detected from the medical image by the region-of-interest detecting unit to be displayed in a manner of emphasized display and changes the emphasized display in accordance with the cumulative detection time period. The display device displays the medical image to which the emphasized display is applied.

A method for operating a medical image processing apparatus of the present invention includes a step of, with a medical image acquiring unit, acquiring a medical image, the medical image being obtained through imaging of an observation target performed by an imaging device; a step of, with a region-of-interest detecting unit, detecting a region of interest in the observation target from the medical image acquired by the medical image acquiring unit; a step of, with a cumulative detection time period measuring unit, measuring a cumulative detection time period during which the region of interest remains detected; and a step of, with a display control unit, causing the region of interest detected from the medical image by the region-of-interest detecting unit to be displayed in a manner of emphasized display and changing the emphasized display in accordance with the cumulative detection time period.

According to the present invention, it is possible to prevent display based on detection of a region of interest from hindering observation of a medical image.

DESCRIPTION OF THE PREFERRED EMBODIMENTS

First Embodiment

Figure 1:
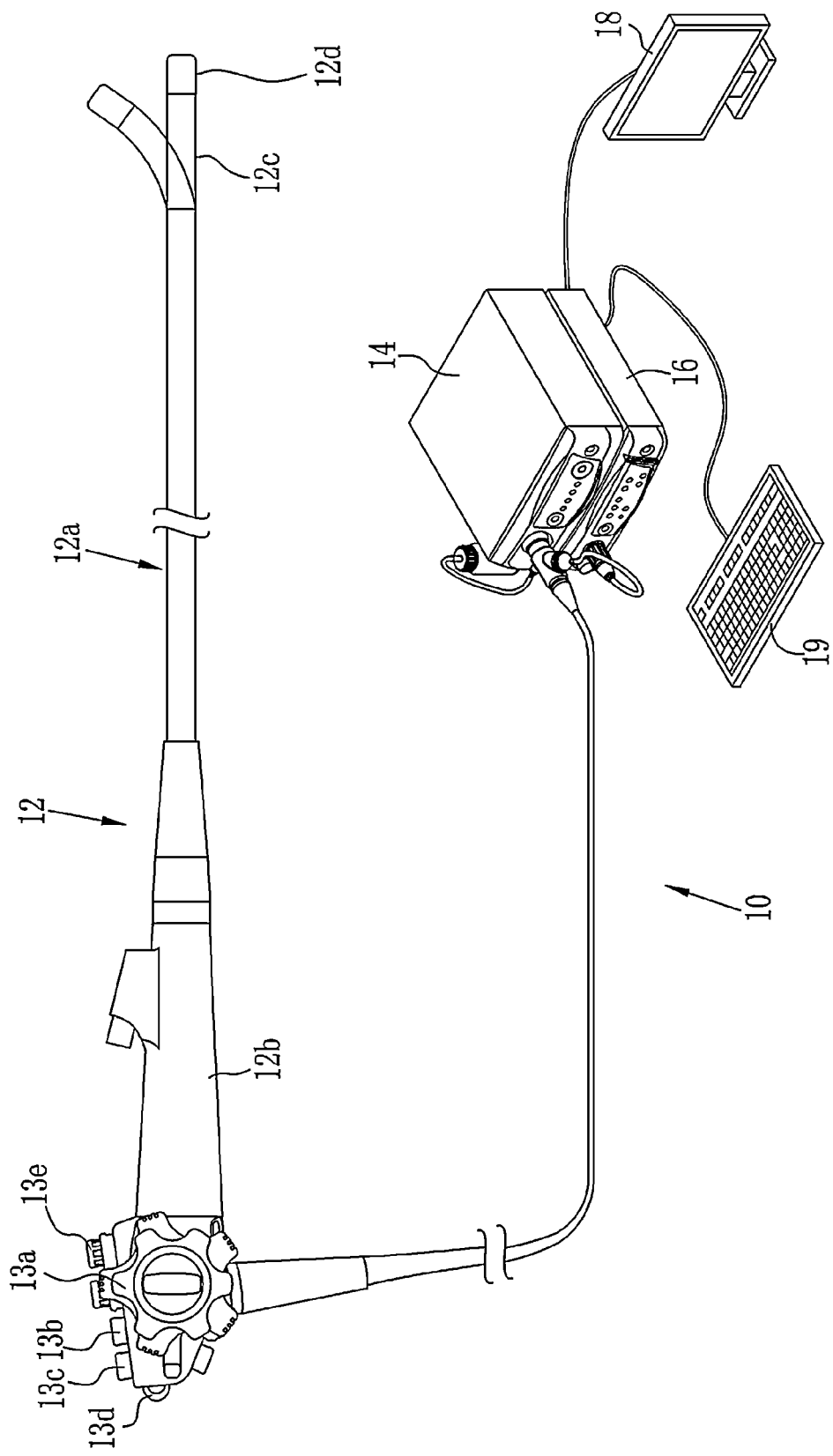
FIG. 1 is an external appearance diagram of an endoscope system.

As illustrated in FIG. 1, an endoscope system 10 has an endoscope 12, a light source device 14, a processor device 16, a monitor 18 (display device), and a console 19. The endoscope 12 is optically connected to the light source device 14 and is electrically connected to the processor device 16. The endoscope 12 has an insertion section 12a to be inserted into a subject, an operation section 12b provided at a base end portion of the insertion section 12a, and a bending portion 12c and a distal end portion 12d that are provided on a distal end side of the insertion section 12a. Operating of an angle knob 13a of the operation section 12b causes the bending portion 12c to perform a bending operation. The bending operation causes the distal end portion 12d to be directed in a desired direction.

The distal end portion 12d has, on the distal end surface thereof, an illumination window, an observation window, an air/water supply nozzle, and a forceps port (any of them is not illustrated). The illumination window is for irradiating an observation portion with illumination light. The observation window is for capturing light from the observation portion. The air/water supply nozzle is for washing the illumination window and the observation window. The forceps port is for performing various treatments by using a treatment tool such as forceps or an electric scalpel.

The operation section 12b is provided with, in addition to the angle knob 13a, a still image acquiring unit 13b to be used for an operation of acquiring a still image, a mode switching unit 13c to be used for an operation of switching an observation mode, a zoom operation unit 13d to be used for an operation of changing zoom magnification, and an air/water supply operation unit 13e. The still image acquiring unit 13b is capable of performing a freeze operation of displaying a still image of an observation target on the monitor 18 and a release operation of storing a still image in storage. The air/water supply operation unit 13e is capable of performing an ejection operation of ejecting air or liquid from the air/water supply nozzle of the distal end portion 12d to wash the illumination window and the observation window.

The endoscope system 10 has a normal mode, a special mode, and a region-of-interest detection mode as observation modes. When the observation mode is the normal mode, normal light generated by combining light beams of a plurality of colors at a light amount ratio Lc for the normal mode is emitted. When the observation mode is the special mode, special light generated by combining light beams of a plurality of colors at a light amount ratio Ls for the special mode is emitted.

When the observation mode is the region-of-interest detection mode, illumination light for the region-of-interest detection mode is emitted. In this embodiment, normal light is emitted as the illumination light for the region-of-interest detection mode. Alternatively, special light may be emitted.

The processor device 16 is electrically connected to the monitor 18 and the console 19. The monitor 18 outputs and displays an image of an observation target, information accompanying the image, and so forth. The console 19 functions as a user interface that receives an input operation for designating a region of interest (ROI), setting a function, or the like.

Figure 2:
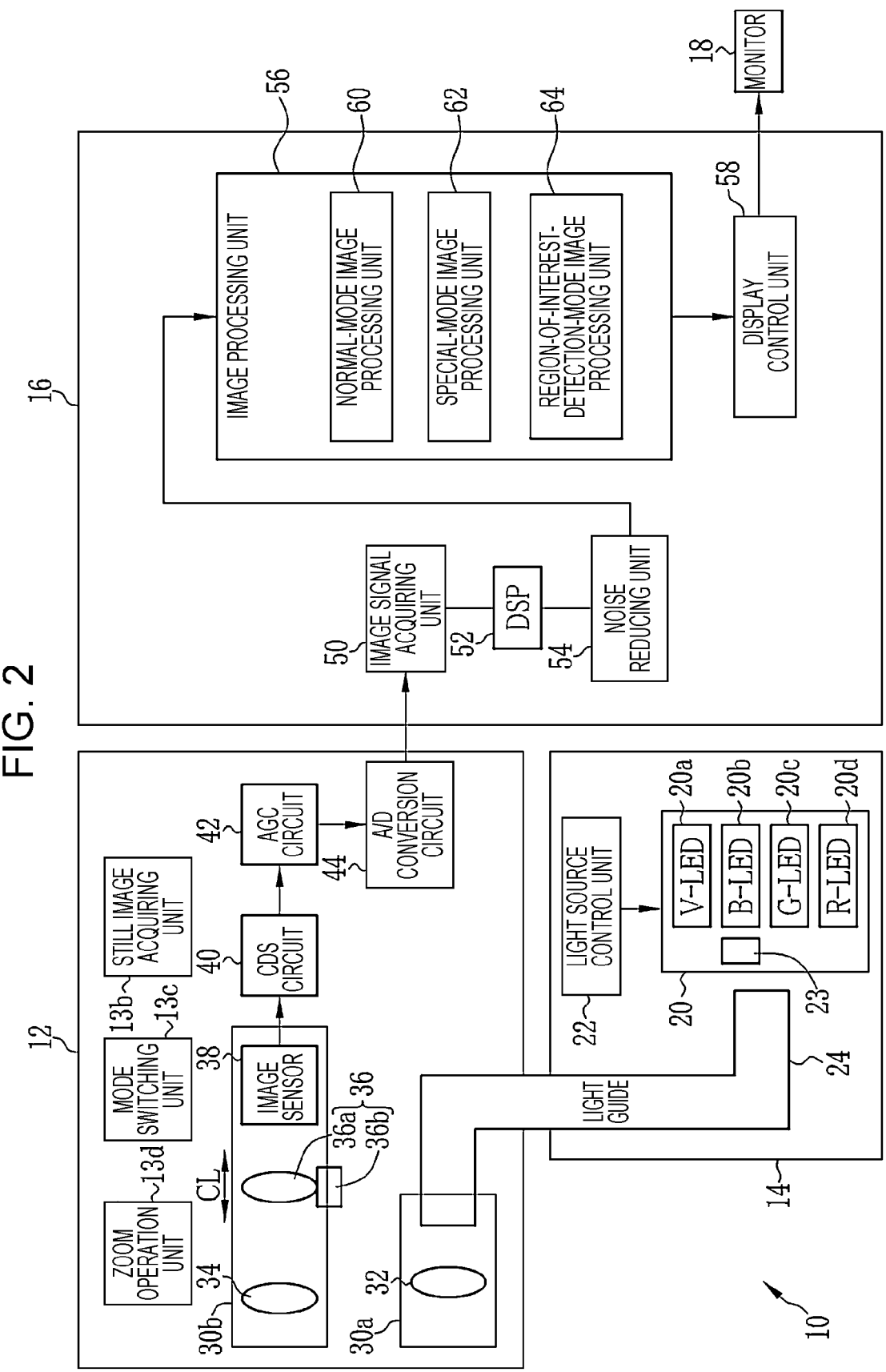
FIG. 2 is a block diagram illustrating the functions of the endoscope system according to a first embodiment including a plurality of LED light sources.

As illustrated in FIG. 2, the light source device 14 includes a light source unit 20 that emits illumination light to be used to illuminate an observation target, and a light source control unit 22 that controls the light source unit 20. The light source unit 20 is a semiconductor light source, such as light emitting diodes (LEDs) of a plurality of colors. The light source control unit 22 turns ON/OFF the LEDs or the like and adjusts driving currents and driving voltages for the LEDs or the like, thereby controlling the amount of illumination light to be emitted. In addition, the light source control unit 22 controls the wavelength range of the illumination light by, for example, changing an optical filter.

Figure 3:
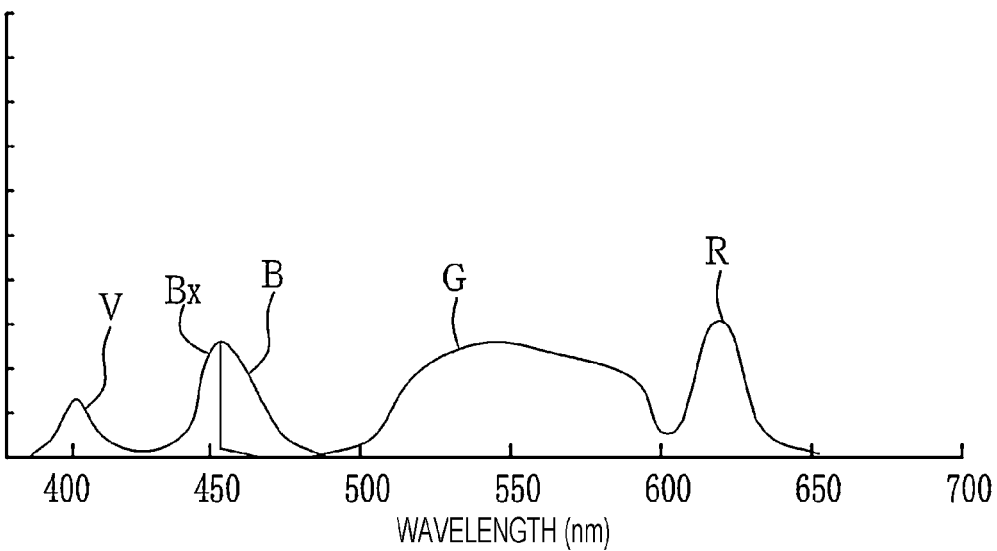
FIG. 3 is a graph illustrating a spectrum of violet light V, blue light B, blue light Bx, green light G, and red light R.

In the first embodiment, the light source unit 20 has LEDs of four colors: a violet light emitting diode (V-LED) 20a; a blue light emitting diode (B-LED) 20b; a green light emitting diode (G-LED) 20c; and a red light emitting diode (R-LED) 20d, and a wavelength cut filter 23. As illustrated in FIG. 3, the V-LED 20a emits violet light V in a wavelength range of 380 nm to 420 nm.

The B-LED 20b emits blue light B in a wavelength range of 420 nm to 500 nm. Of the blue light B emitted by the B-LED 20b, at least the longer wavelength side with respect to a peak wavelength of 460 nm is cut off by the wavelength cut filter 23. Accordingly, blue light Bx that has passed through the wavelength cut filter 23 is in a wavelength range of 420 nm to 460 nm. The light in the wavelength range on the longer wavelength side with respect to 460 nm is cut off because the light in the wavelength range on the longer wavelength side with respect to 460 nm is a factor in decreasing the contrast of blood vessels as an observation target. The wavelength cut filter 23 may decrease the amount of light in the wavelength range on the longer wavelength side with respect to 460 nm instead of cutting off the light in the wavelength range on the longer wavelength side with respect to 460 nm.

The G-LED 20c emits green light G in a wavelength range of 480 nm to 600 nm. The R-LED 20d emits red light R in a wavelength range of 600 nm to 650 nm. The light emitted by each of the LEDs 20a to 20d may have a center wavelength and a peak wavelength that are identical to or different from each other.

The light source control unit 22 controls ON/OFF of each of the LEDs 20a to 20d and the amount of light emission in an ON state independently from each other, thereby adjusting the emission timing, emission period, amount of light, and spectrum of illumination light. The ON/OFF control by the light source control unit 22 varies according to an observation mode. A reference brightness can be set by a brightness setting unit of the light source device 14, the console 19, or the like.

Figure 4:
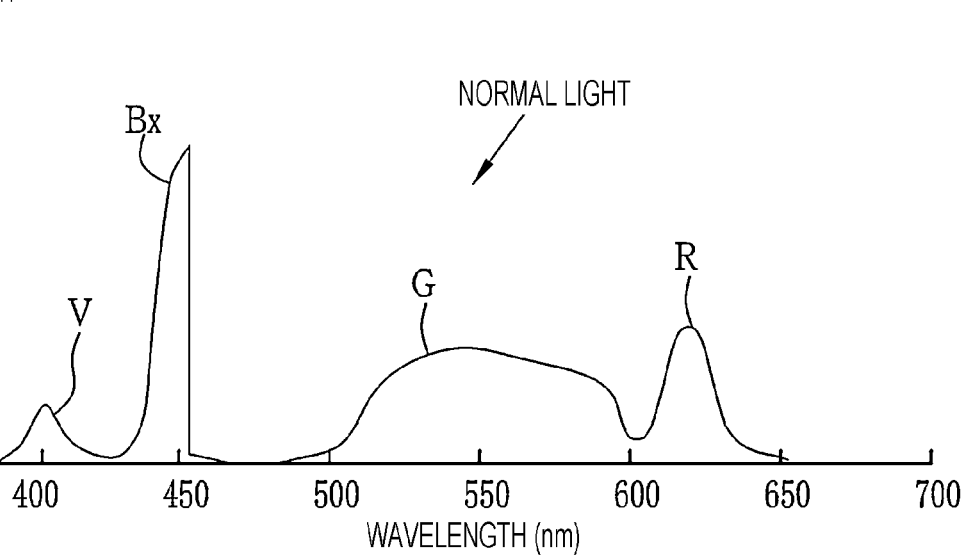
FIG. 4 is a graph illustrating a spectrum of normal light according to the first embodiment.

In the normal mode or the region-of-interest detection mode, the light source control unit 22 turns on all of the V-LED 20a, the B-LED 20b, the G-LED 20c, and the R-LED 20d. At this time, as illustrated in FIG. 4, the light amount ratio Lc among the violet light V, the blue light Bx, the green light G, and the red light R is set such that the peak intensity of the blue light Bx is higher than each of the peak intensities of the violet light V, the green light G, and the red light R. Accordingly, in the normal mode or the region-of-interest detection mode, the light source device 14 emits, as normal light, multicolor light for the normal mode or the region-of-interest detection mode including the violet light V, the blue light Bx, the green light G, and the red light R. The normal light has a certain intensity or more in the blue range to the red range and is thus substantially white.

Figure 5:
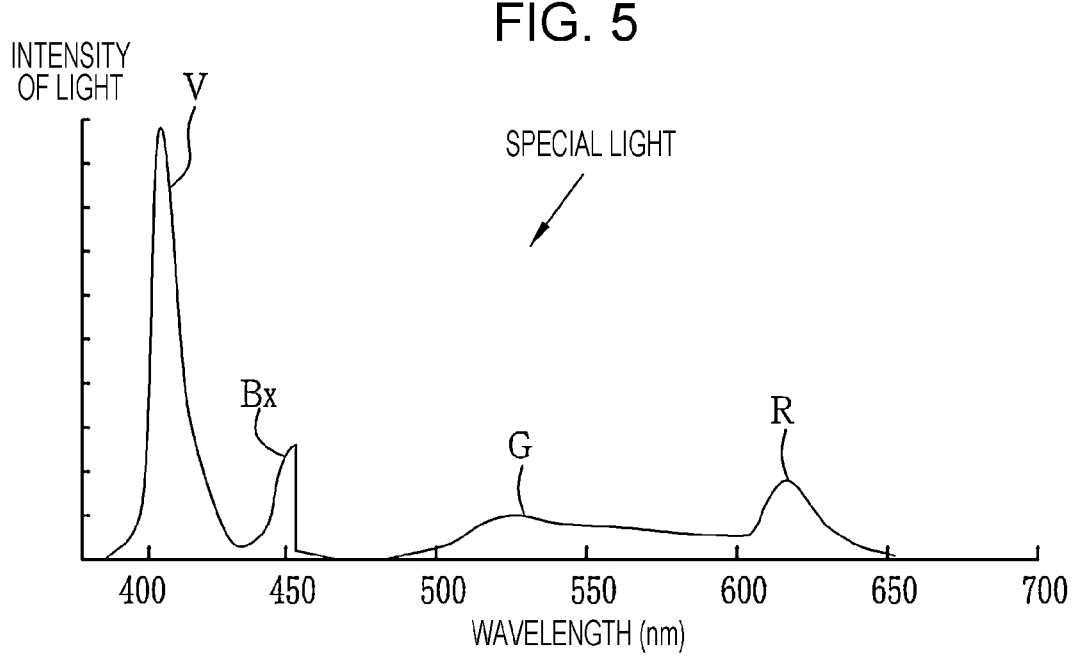
FIG. 5 is a graph illustrating a spectrum of special light according to the first embodiment.

In the special mode, the light source control unit 22 turns on all of the V-LED 20a, the B-LED 20b, the G-LED 20c, and the R-LED 20d. At this time, as illustrated in FIG. 5, the light amount ratio Ls among the violet light V, the blue light Bx, the green light G, and the red light R is set such that the peak intensity of the violet light V is higher than each of the peak intensities of the blue light Bx, the green light G, and the red light R and such that each of the peak intensities of the green light G and the red light R is lower than each of the peak intensities of the violet light V and the blue light Bx. Accordingly, in the special mode, the light source device 14 emits, as special light, multicolor light for the special mode including the violet light V, the blue light Bx, the green light G, and the red light R. The special light has a large proportion of the violet light V and is thus bluish. The special light does not necessarily need to include light of all the four colors, and may include light from at least one of the LEDs 20a to 20d of four colors. Preferably, the special light may have a main wavelength range, for example, a peak wavelength or a center wavelength, in a range that is 450 nm or less.

As illustrated in FIG. 2, the illumination light emitted by the light source unit 20 passes through a light path coupling unit (not illustrated) formed of a mirror, a lens, and the like and then enters a light guide 24 that extends through the insertion section 12a. The light guide 24 is built in the endoscope 12 and a universal cord, and causes the illumination light to propagate to the distal end portion 12d of the endoscope 12. The universal cord is a cord that connects the endoscope 12 to the light source device 14 and the processor device 16. A multimode fiber may be used as the light guide 24. As an example, a small-diameter fiber cable with a core diameter of 105 μm, a clad diameter of 125 μm, and a diameter including a protective layer serving as an outer cover of ϕ0.3 mm to ϕ0.5 mm may be used as the light guide 24.

The distal end portion 12d of the endoscope 12 is provided with an illumination optical system 30a and an imaging optical system 30b. The illumination optical system 30a has an illumination lens 32. An observation target is illuminated, via the illumination lens 32, with illumination light that has propagated through the light guide 24. The imaging optical system 30b has an objective lens 34, a magnifying optical system 36, and an image sensor 38 (corresponding to the "imaging device" of the present invention). Various types of light, such as reflected light, scattered light, and fluorescence from the observation target, enters the image sensor 38 through the objective lens 34 and the magnifying optical system 36. Accordingly, an image of the observation target is formed on the image sensor 38.

The magnifying optical system 36 includes a zoom lens 36a that magnifies an observation target, and a lens driving unit 36b that moves the zoom lens 36a in optical-axis directions CL. The zoom lens 36a is freely moved between a telephoto end and a wide end in accordance with zoom control by the lens driving unit 36b, thereby magnifying or demagnifying the image of the observation target formed on the image sensor 38.

The image sensor 38 is a color image sensor that performs imaging of an observation target irradiated with illumination light. Each of the pixels of the image sensor 38 is provided with a red (R) color filter, a green (G) color filter, or a blue (B) color filter. The image sensor 38 receives violet to blue light by using B pixels provided with the B color filter, receives green light by using G pixels provided with the G color filter, and receives red light by using R pixels provided with the R color filter. The image sensor 38 outputs image signals of individual colors of RGB from the pixels of the individual colors. The image sensor 38 transmits the output image signals to a correlated double sampling (CDS) circuit 40.

In the normal mode or the region-of-interest detection mode, the image sensor 38 performs imaging of an observation target illuminated with normal light, thereby outputting Bc image signals from the B pixels, outputting Gc image signals from the G pixels, and outputting Rc image signals from the R pixels. In the special mode, the image sensor 38 performs imaging of an observation target illuminated with special light, thereby outputting Bs image signals from the B pixels, outputting Gs image signals from the G pixels, and outputting Rs image signals from the R pixels.

A charge coupled device (CCD) image sensor, a complementary metal-oxide semiconductor (CMOS) image sensor, or the like can be used as the image sensor 38. Instead of the image sensor 38 provided with color filters of the primary colors RGB, a complementary-color image sensor including complementary-color filters of cyan (C), magenta (M), yellow (Y), and green (G) may be used. In the case of using the complementary-color image sensor, image signals of four colors CMYG are output. Thus, as a result of converting image signals of four colors CMYG into image signals of three colors RGB by using complementary color to primary color conversion, image signals of individual colors RGB similar to those in the image sensor 38 can be acquired. Alternatively, a monochrome sensor not provided with color filters may be used instead of the image sensor 38.

The CDS circuit 40 performs correlated double sampling (CDS) on analog image signals received from the image sensor 38. The image signals output from the CDS circuit 40 are input to an automatic gain control (AGC) circuit 42. The AGC circuit 42 performs automatic gain control (AGC) on the image signals input thereto. An analog to digital (A/D) conversion circuit 44 converts the analog image signals output from the AGC circuit 42 into digital image signals. The A/D conversion circuit 44 inputs the digital image signals generated through the A/D conversion to the processor device 16.

As illustrated in FIG. 2, the processor device 16 includes an image signal acquiring unit 50 (corresponding to the "medical image acquiring unit" of the present invention), a digital signal processor (DSP) 52, a noise reducing unit 54, an image processing unit 56, and a display control unit 58.

The image signal acquiring unit 50 acquires digital image signals corresponding to an observation mode from the endoscope 12. In the normal mode or the region-of-interest detection mode, the image signal acquiring unit 50 acquires Bc image signals, Gc image signals, and Rc image signals. In the special mode, the image signal acquiring unit 50 acquires Bs image signals, Gs image signals, and Rs image signals. In the region-of-interest detection mode, the image signal acquiring unit 50 acquires Bc image signals, Gc image signals, and Rc image signals of one frame during illumination with normal light, and acquires Bs image signals, Gs image signals, and Rs image signals of one frame during illumination with special light.

The DSP 52 performs various signal processing operations, such as defect correction processing, offset processing, DSP gain correction processing, linear matrix processing, gamma conversion processing, and demosaicing processing, on the image signals acquired by the image signal acquiring unit 50. The defect correction processing corrects a signal of a defective pixel of the image sensor 38. The offset processing removes a dark current component from the image signal that has been subjected to the defect correction processing and sets an accurate zero level. The DSP gain correction processing multiplies the image signal that has been subjected to the offset processing by a specific DSP gain, thereby adjusting the signal level.

The linear matrix processing increases the color reproducibility of the image signal that has been subjected to the DSP gain correction processing. The gamma conversion processing adjusts the brightness and chroma of the image signal that has been subjected to the linear matrix processing. The image signal that has been subjected to the gamma conversion processing is subjected to demosaicing processing (also referred to as isotropic processing or synchronization processing), thereby generating, through interpolation, a signal of a color insufficient in each pixel. The demosaicing processing enables all pixels to have signals of individual colors RGB. The noise reducing unit 54 performs noise reduction processing using, for example, a moving-average method, a median filter method, or the like, on the image signal that has been subjected to the demosaicing processing and so forth in the DSP 52, thereby reducing noise. The image signal that has been subjected to the noise reduction is input to the image processing unit 56.

The image processing unit 56 includes a normal-mode image processing unit 60, a special-mode image processing unit 62, and a region-of-interest-detection-mode image processing unit 64. The normal-mode image processing unit 60 operates when the normal mode is set, and performs color conversion processing, color enhancement processing, and structure enhancement processing on the Bc image signals, Gc image signals, and Rc image signals that have been received. In the color conversion processing, color conversion processing is performed on the RGB image signals by using 3×3 matrix processing, gradation transformation processing, three-dimensional look up table (LUT) processing, and the like.

The color enhancement processing is performed on the RGB image signals that have been subjected to color conversion processing. The structure enhancement processing is processing of enhancing the structure of an observation target and is performed on the RGB image signals that have been subjected to the color enhancement processing. The above-described various image processing operations enable a normal image to be acquired. The normal image is an image acquired on the basis of normal light including the violet light V, the blue light Bx, the green light G, and the red light R with a well-balanced ratio, and is thus an image with natural colors. The normal image is input to the display control unit 58.

The special-mode image processing unit 62 operates when the special mode is set. The special-mode image processing unit 62 performs color conversion processing, color enhancement processing, and structure enhancement processing on the Bs image signals, Gs image signals, and Rs image signals that have been received. The processing performed in the color conversion processing, the color enhancement processing, and the structure enhancement processing is similar to that performed by the normal-mode image processing unit 60. The above-described various image processing operations enable a special image to be acquired. The special image is an image acquired on the basis of special light in which the amount of the violet light V having a high hemoglobin absorption coefficient of blood vessels is larger than the amount of the blue light Bx, the green light G, and the red light R, and thus the resolution of a blood vessel structure and a gland duct structure is higher than that of other structures. The special image is input to the display control unit 58.

Figure 6:
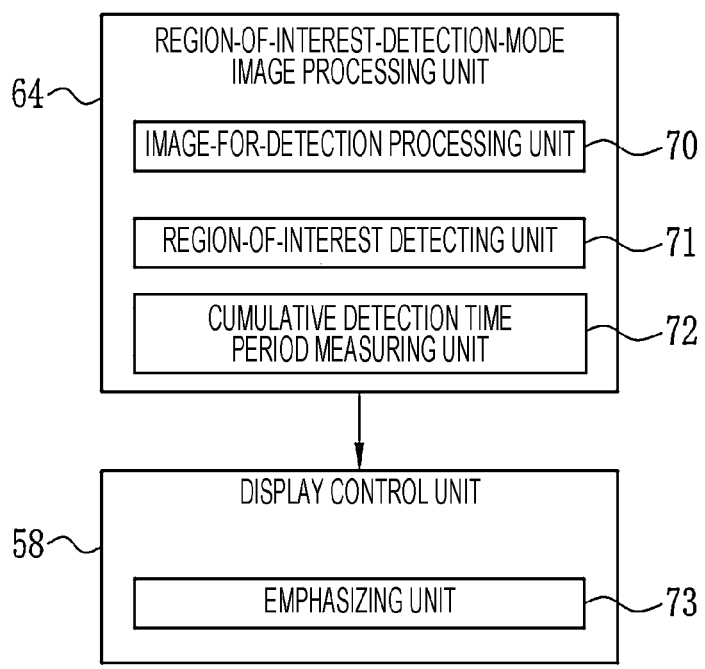
FIG. 6 is a block diagram illustrating functions of a region-of-interest-detection-mode image processing unit and a display control unit.

The region-of-interest-detection-mode image processing unit 64 operates when the region-of-interest detection mode is set. As illustrated in FIG. 6, the region-of-interest-detection-mode image processing unit 64 has an image-for-detection processing unit 70, a region-of-interest detecting unit 71, and a cumulative detection time period measuring unit 72. The image-for-detection processing unit 70 performs image processing similar to that performed by the normal-mode image processing unit 60, such as color conversion processing, on the Bc image signals, Gc image signals, and Rc image signals that have been received, thereby sequentially acquiring endoscopic images.

The region-of-interest detecting unit 71 analyzes an endoscopic image and performs region-of-interest detection processing for detecting a region of interest in an observation target. In this embodiment, the region-of-interest detecting unit 71 detects, as a region of interest, a lesion portion (for example, a tumor, an inflammation, or the like) in the observation target. In this case, the region-of-interest detecting unit 71 first divides the endoscopic image into a plurality of small regions, for example, square regions each formed of a certain number of pixels. Subsequently, the region-of-interest detecting unit 71 calculates image feature quantities from the divided endoscopic image. Subsequently, the region-of-interest detecting unit 71 recognizes, on the basis of the calculated feature quantities, whether or not each of the small regions is a lesion portion. Preferably, such recognition processing may be a machine learning algorithm such as a convolutional neural network or deep learning.

Preferably, a feature quantity calculated from an endoscopic image by the region-of-interest detecting unit 71 may be the shape or color of a predetermined portion in an observation target, or an index value acquired from the shape or color. Preferably, for example, the feature quantity may be at least any one of the density of a blood vessel, the shape of a blood vessel, the number of branches of a blood vessel, the thickness of a blood vessel, the length of a blood vessel, the degree of meandering of a blood vessel, the depth of a blood vessel, the shape of a gland duct, the shape of an opening portion of a gland duct, the length of a gland duct, the degree of meandering of a gland duct, or color information, or the value of a combination of two or more of them.

Finally, the region-of-interest detecting unit 71 extracts a group of small regions specified as the same type as one lesion portion. The region-of-interest detecting unit 71 associates information indicating the position, size, type, and the like of the extracted lesion portion as a detection result with the endoscopic image. The region-of-interest-detection-mode image processing unit 64 outputs the endoscopic image associated with the detection result to the display control unit 58.

On the other hand, in a case where the region-of-interest detecting unit 71 detects a region of interest, the cumulative detection time period measuring unit 72 measures a cumulative detection time period during which the region of interest remains detected. For example, the cumulative detection time period measuring unit 72 measures, using a counter, the time period during which the region of interest remains detected by the region-of-interest detecting unit 71. The initial value of the counter is 0. The counter value is incremented by one (the counter value+1) every time a clock signal of a predetermined cycle is input, with the start of detection of the region of interest by the region-of-interest detecting unit 71 being a base point. Incrementing of the counter value by one corresponds to measuring of a cumulative detection time period in every cycle of the counter.

In this case, the cumulative detection time period measuring unit 72 outputs the counter value to the display control unit 58. At the start of detection of a region of interest by the region-of-interest detecting unit 71, the cumulative detection time period measuring unit 72 outputs a counter value of 0 as a cumulative detection time period together with the endoscopic image (the image in which the region of interest is started to be detected). While the region of interest remains detected in the observation target, the cumulative detection time period measuring unit 72 continues outputting a counter value to the display control unit 58.

The display control unit 58 performs display control for displaying an image or data from the image processing unit 56 on the monitor 18. When the normal mode is set, the display control unit 58 performs control to display a normal image on the monitor 18. When the special mode is set, the display control unit 58 performs control to display a special image on the monitor 18.

When the region-of-interest detection mode is set, the display control unit 58 causes a region of interest detected from an endoscopic image by the region-of-interest detecting unit 71 to be displayed in a manner of emphasized display, and changes the emphasized display in accordance with the cumulative detection time period measured by the cumulative detection time period measuring unit 72. The display control unit 58 includes an emphasizing unit 73. On the basis of the endoscopic image output from the region-of-interest-detection-mode image processing unit 64 and the detection result associated with the endoscopic image, the emphasizing unit 73 applies emphasized display for emphasizing the region of interest to the endoscopic image.

Figure 7:
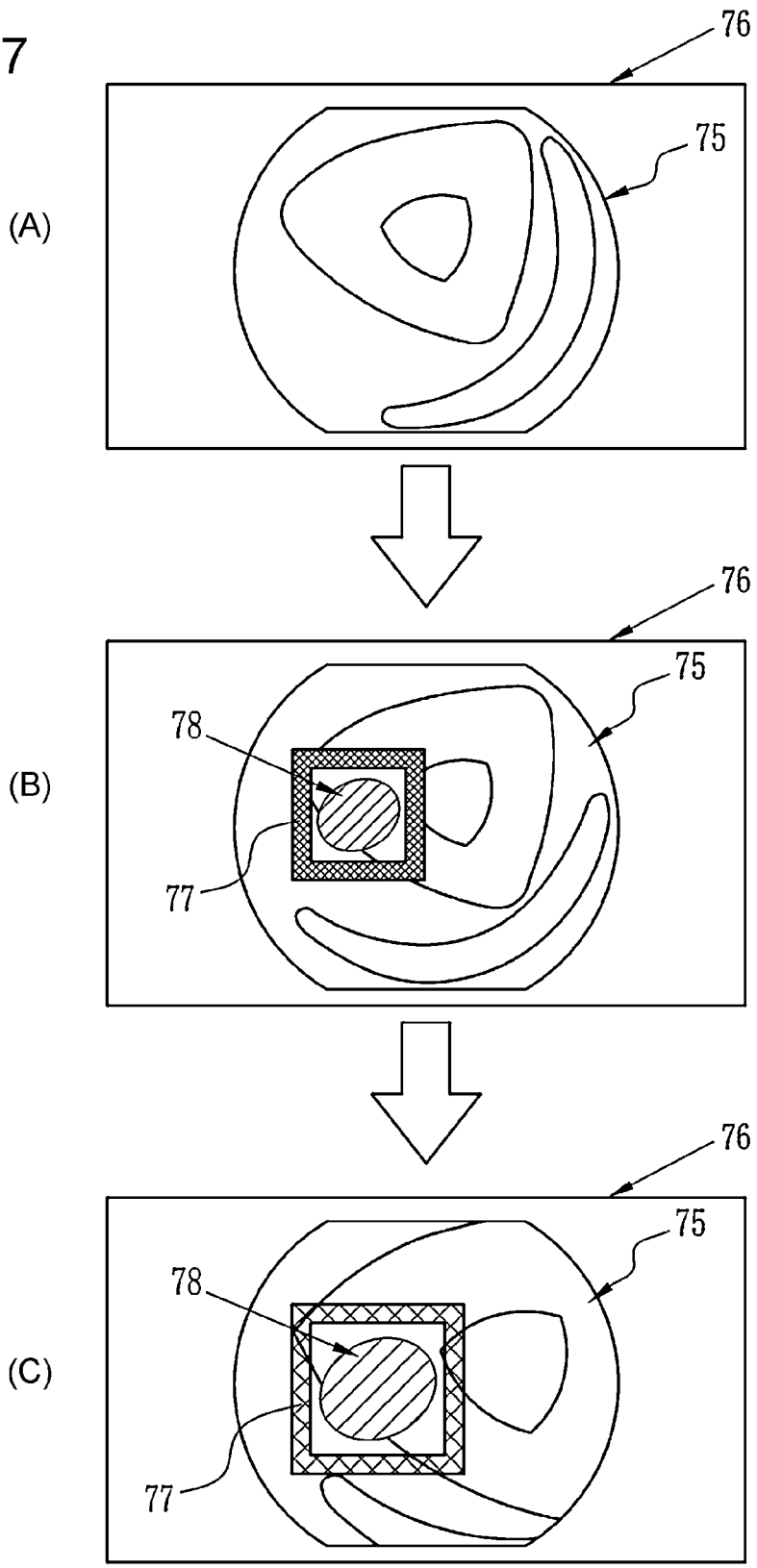
FIG. 7 is an explanatory diagram illustrating an example of a display screen in a case where the display control unit performs emphasized display of a region of interest and illustrating changes in the display screen in chronological order.

As illustrated in part (A) of FIG. 7, in a case where a region of interest in an observation target is not detected, the display control unit 58 sequentially acquires endoscopic images 75 (images similar to normal images) captured by the image sensor 38 and processed by the region-of-interest-detection-mode image processing unit 64, and displays the endoscopic images 75 in real time on a display screen 76 of the monitor 18. In this case, emphasized display is not performed obviously.

In a case where a lesion portion as a region of interest is detected in the observation target, that is, in a case where a detection result is associated with the endoscopic image 75 by the region-of-interest-detection-mode image processing unit 64, the emphasizing unit 73 generates an image of a figure that is based on information indicating the position and size of the lesion portion in the detection result associated with the endoscopic image 75. Subsequently, the emphasizing unit 73 superimposes the figure for emphasized display on the position of the lesion portion in the endoscopic image 75. In this embodiment, the display control unit 58 causes a rectangular-frame-shaped FIG. 77 surrounding a lesion portion 78 to be displayed for emphasized display, as illustrated in parts (B) and (C) of FIG. 7.

The display control unit 58 causes the FIG. 77 to be displayed for emphasized display and changes the emphasized display in accordance with the cumulative detection time period measured by the cumulative detection time period measuring unit 72, as described above. Specifically, the display control unit 58 changes the transparency of the FIG. 77 in accordance with the cumulative detection time period. As the transparency increases, the endoscopic image 75 is more clearly seen through the FIG. 77. When the transparency is 100%, the FIG. 77 is completely transparent and is invisible. When the transparency is 0%, the portion of the endoscopic image 75 on which the FIG. 77 is superimposed is completely invisible. As illustrated in part (B) of FIG. 7, at the start of detection of the lesion portion 78 as a region of interest, the amount of emphasis of the FIG. 77 is maximized, that is, the transparency of the FIG. 77 is set to 0%. In this case, the cumulative detection time period measured by the cumulative detection time period measuring unit 72 is 0.

As illustrated in part (C) of FIG. 7, as the cumulative detection time period increases, the amount of emphasis of the FIG. 77 is gradually decreased, that is, the transparency of the FIG. 77 is gradually increased. In parts (B) and (C) of FIG. 7, for convenience of illustration, the transparency of the FIG. 77 is expressed by the density of hatching applied to the FIG. 77. The density of hatching is higher in the FIG. 77 in part (B) of FIG. 7 than in the FIG. 77 in part (C) of FIG. 7. In this case, the transparency in part (C) of FIG. 7 is proportional to the cumulative detection time period (counter value) that is output at the same time when the endoscopic image 75 illustrated in part (C) of FIG. 7 is output.

On the other hand, in a case where the lesion portion as a region of interest is not detected any longer after the state illustrated in part (C) of FIG. 7, that is, in a case where there is no detection result associated with the endoscopic image 75 by the region-of-interest-detection-mode image processing unit 64, the cumulative detection time period measuring unit 72 stops measuring the cumulative detection time period, and the emphasizing unit 73 stops emphasized display. Subsequently, the cumulative detection time period measuring unit 72 resets the cumulative detection time period. In a case where a lesion portion as a region of interest is detected next time, the cumulative detection time period measuring unit 72 starts measuring the cumulative detection time period from the initial value (a counter value of 0).

Figure 8:
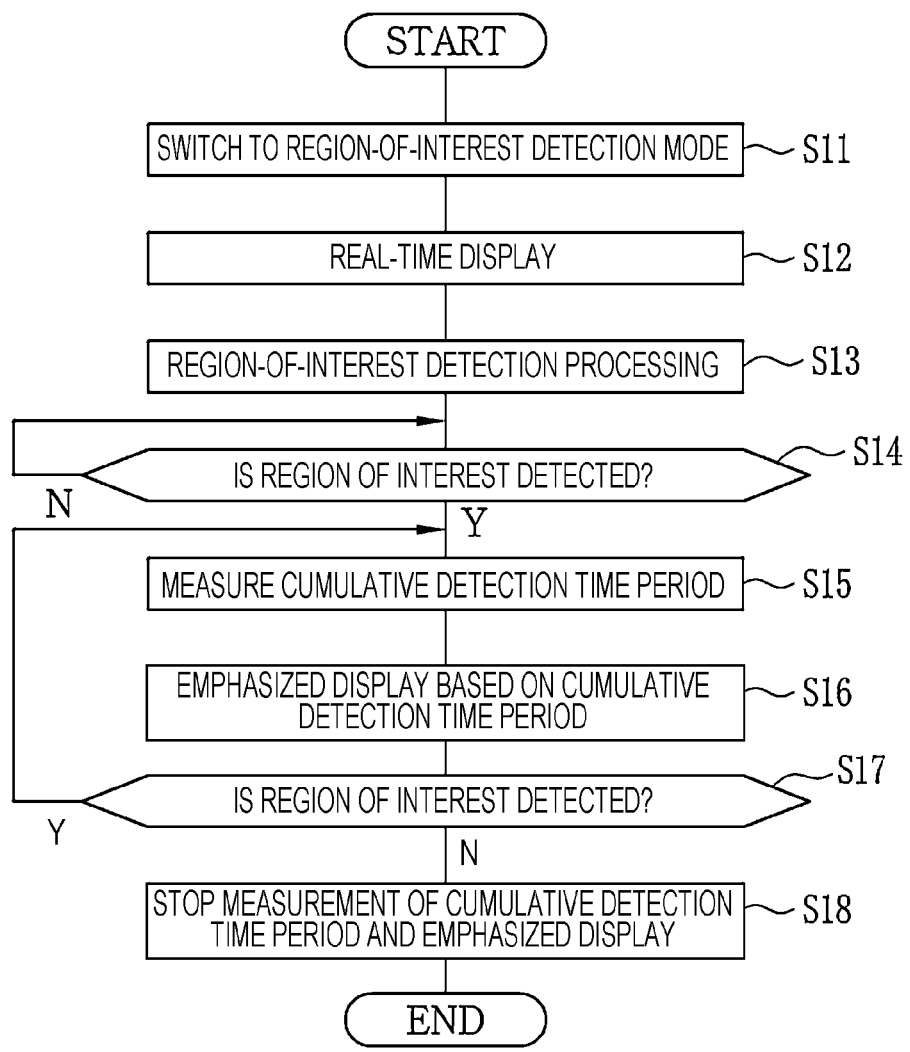
FIG. 8 is a flowchart illustrating a flow of a region-of-interest detection mode.

Next, a flow of the region-of-interest detection mode will be described with reference to the flowchart illustrated in FIG. 8. A medical doctor who is a user operates the mode switching unit 13c to switch the mode to the region-of-interest detection mode (S11). Accordingly, an observation target is illuminated with illumination light for the region-of-interest detection mode. The image sensor 38 performs imaging of the observation target illuminated with the illumination light for the region-of-interest detection mode, and thereby an endoscopic image is acquired. In the region-of-interest detection mode, the display control unit 58 displays the endoscopic image 75 on the display screen 76 of the monitor 18 in real time (S12).

During real-time display in the region-of-interest detection mode, the region-of-interest detecting unit 71 performs region-of-interest detection processing for detecting a region of interest in the observation target on the acquired endoscopic image (S13). In a case where a region of interest is detected (Y in S14), a detection result is output in association with the endoscopic image, and the cumulative detection time period measuring unit 72 measures and outputs a cumulative detection time period during which the region of interest remains detected (S15).

Subsequently, the emphasizing unit 73 causes the FIG. 77 to be displayed for emphasized display on the basis of the detection result and the cumulative detection time period and changes the FIG. 77 in accordance with the cumulative detection time period measured by the cumulative detection time period measuring unit 72 (S16). The measurement of the cumulative detection time period and the emphasized display based on the cumulative detection time period are continued as long as the region of interest remains detected (Y in S17). On the other hand, in a case where the region of interest is not detected any longer (N in S17), the measurement of the cumulative detection time period and the emphasized display are stopped (S18). In this way, while the region of interest remains detected, emphasized display based on the cumulative detection time period is performed, and thus the medical doctor is able to perform observation while easily recognizing the region of interest. When the amount of emphasis of the emphasized display gradually decreases in accordance with the cumulative detection time period and the region of interest is not detected from the observation target, the emphasized display ends. Thus, the emphasized display does not hinder the observation performed by the medical doctor.

Second Embodiment

Figure 9:
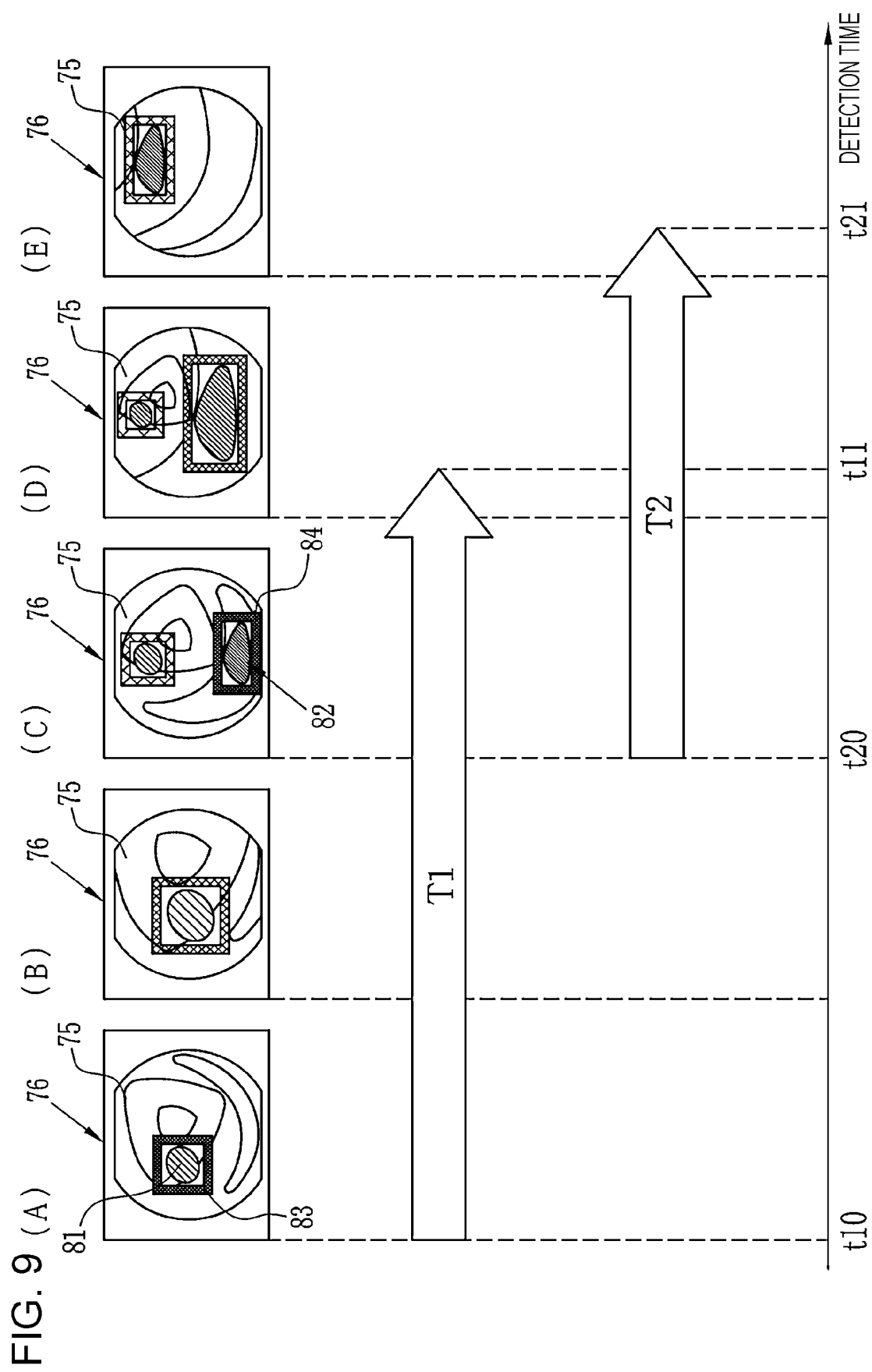
FIG. 9 is an explanatory diagram illustrating a relationship between a cumulative detection time period and emphasized display in a case where the display control unit performs emphasized display of a plurality of regions of interest according to a second embodiment.
Figure 10:
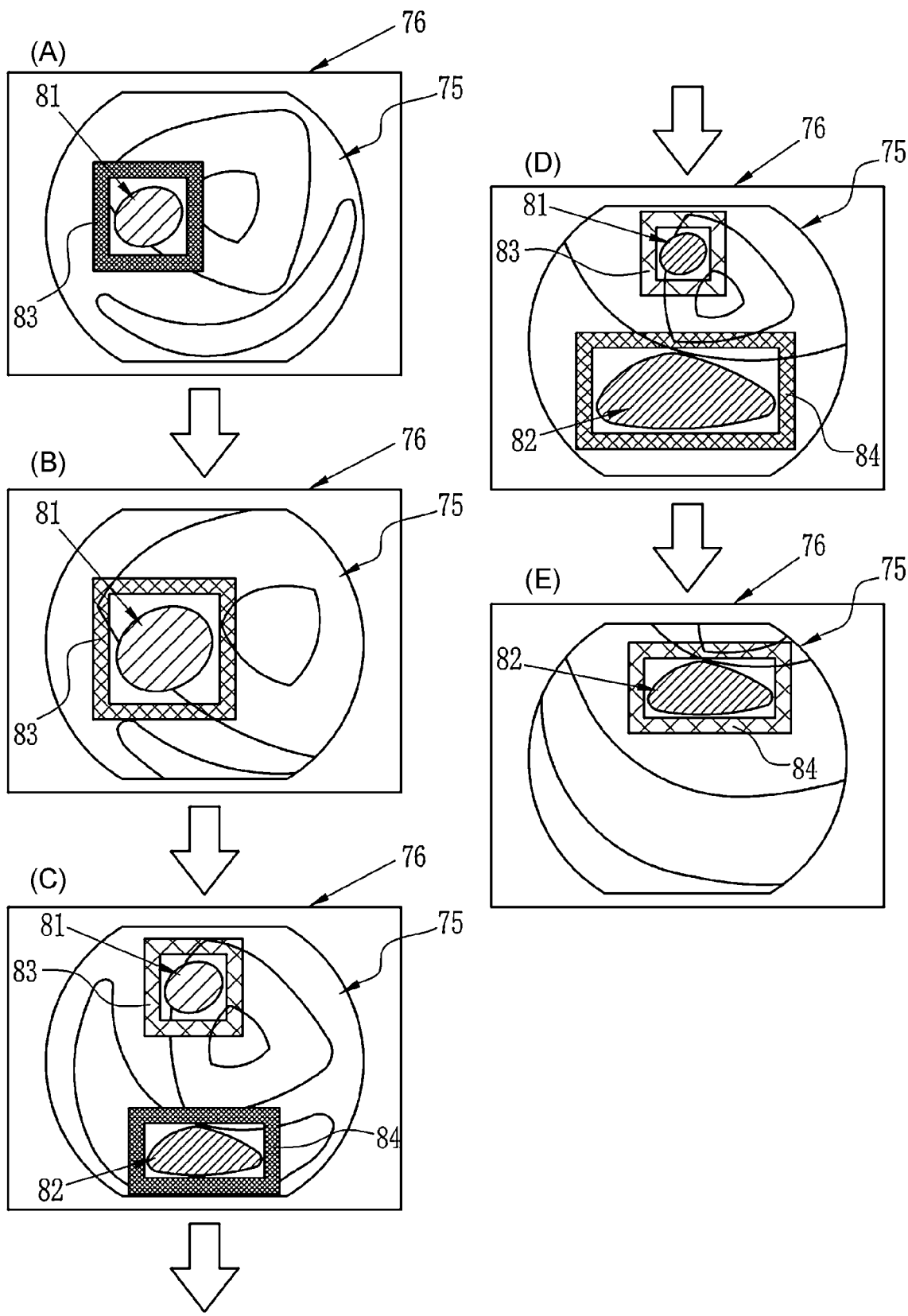
FIG. 10 is an explanatory diagram corresponding to the display screens illustrated in FIG. 9 and illustrating changes in the display screen in chronological order.

In the above-described first embodiment, a description has been given, as an example, a case where only one region of interest is detected in an observation target. Alternatively, in a case where a plurality of regions of interest are detected in an observation target, cumulative detection time periods of the respective detected regions of interest may be measured, and the display control unit 58 may change emphasized display in accordance with the cumulative detection time periods of the respective regions of interest. FIG. 9 and FIG. 10 illustrate, as an example, a case where two regions of interest are detected while endoscopic images are sequentially acquired through imaging of an observation target performed by the image sensor 38.

In this case, a first lesion portion 81 is detected first as a region of interest as illustrated in parts (A) to (D) of FIG. 9, and then a second lesion portion 82 is detected as a region of interest as illustrated in parts (C) to (E) of FIG. 9. The endoscopic images illustrated in parts (A) to (E) of FIG. 9 and the endoscopic images illustrated in parts (A) to (E) of FIG. 10 are identical to each other. The endoscopic images are arranged in chronological order in which the images have been acquired through imaging performed by the image sensor 38. The cumulative detection time period measuring unit 72 measures the cumulative detection time periods of the first lesion portion 81 and the second lesion portion 82.

Time t10 at which the endoscopic image 75 illustrated in part (A) of FIG. 9 and part (A) of FIG. 10 is acquired corresponds to the start of detection of the first lesion portion 81. At time t10, a first cumulative detection time period T1 is 0, and the amount of emphasis of a frame-shaped FIG. 83 for emphasized display of the first lesion portion 81 is maximum. At time t10, the cumulative detection time period measuring unit 72 starts measuring the first cumulative detection time period T1.

As illustrated in parts (A) to (D) of FIG. 9 and parts (A) to (D) of FIG. 10, the amount of emphasis of the FIG. 83 gradually decreases as the first cumulative detection time period T1 increases, as in the above-described first embodiment. Finally, at time t11, which is after the endoscopic image 75 illustrated in part (D) of FIG. 9 and part (D) of FIG. 10 is acquired, the first lesion portion 81 is not seen in the observation target. Accordingly, the first lesion portion 81 is not detected any longer by the region-of-interest detecting unit 71. That is, at time t11, the measurement of the first cumulative detection time period T1 is stopped, and the FIG. 83 for emphasized display is not displayed. The cumulative detection time period measuring unit 72 resets the first cumulative detection time period T1.

On the other hand, time t20 at which the endoscopic image 75 illustrated in part (C) of FIG. 9 and part (C) of FIG. 10 is acquired corresponds to the start of detection of the second lesion portion 82. At time t20, a second cumulative detection time period T2 is 0, and the amount of emphasis of a frame-shaped FIG. 84 for emphasized display of the second lesion portion 82 is maximum. At time t20, the cumulative detection time period measuring unit 72 starts measuring the second cumulative detection time period T2. As illustrated in parts (C) to (E) of FIG. 9 and parts (C) to (E) of FIG. 10, the amount of emphasis of the FIG. 84 gradually decreases as the second cumulative detection time period T2 increases. At time t21, which is after the endoscopic image 75 illustrated in part (E) of FIG. 9 and part (E) of FIG. 10 is acquired, the second lesion portion 82 is not seen in the endoscopic image 75. Accordingly, at time t21, the measurement of the second cumulative detection time period T2 is stopped, and the FIG. 84 for emphasized display is not displayed. The cumulative detection time period measuring unit 72 resets the second cumulative detection time period T2.

As described above, in a case where the first and second lesion portions 81 and 82 are detected from the endoscopic image 75, the cumulative detection time periods T1 and T2 are measured for the detected first and second lesion portions 81 and 82, respectively, and the display control unit 58 changes the emphasized display in accordance with the cumulative detection time periods T1 and T2 of the respective regions of interest. Thus, a medical doctor who is a user is able to observe the first and second lesion portions 81 and 82 by reliably distinguishing them from each other and is able to increase the efficiency of observation. Furthermore, the emphasized display is almost finished when the observation of a lesion portion is finished, and thus oversight of another lesion portion can be prevented. For example, in a case where the second lesion portion 82 enters a filed of view after the observation of the first lesion portion 81, if the amounts of emphasis of the lesion portions are equal to each other, the first lesion portion 81 may be focused on whereas the second lesion portion 82 may be overlooked. In the present invention, the amount of emphasis of the first lesion portion 81 has been decreased when the observation of the first lesion portion 81 is finished. Thus, the emphasized display of the second lesion portion 82 is conspicuous, and the oversight of the second lesion portion 82 can be prevented.

Third Embodiment

In the above-described first and second embodiments, in a case where a region of interest is not detected any longer, the measurement of the cumulative detection time period is stopped and the measurement of the cumulative detection time period is reset. Alternatively, in a case where a newly detected region of interest is determined to be identical to any one of previously detected regions of interest, the cumulative detection time period of the previous region of interest that has been determined to be identical to the newly detected region of interest may be taken over and measured.

Figure 11:
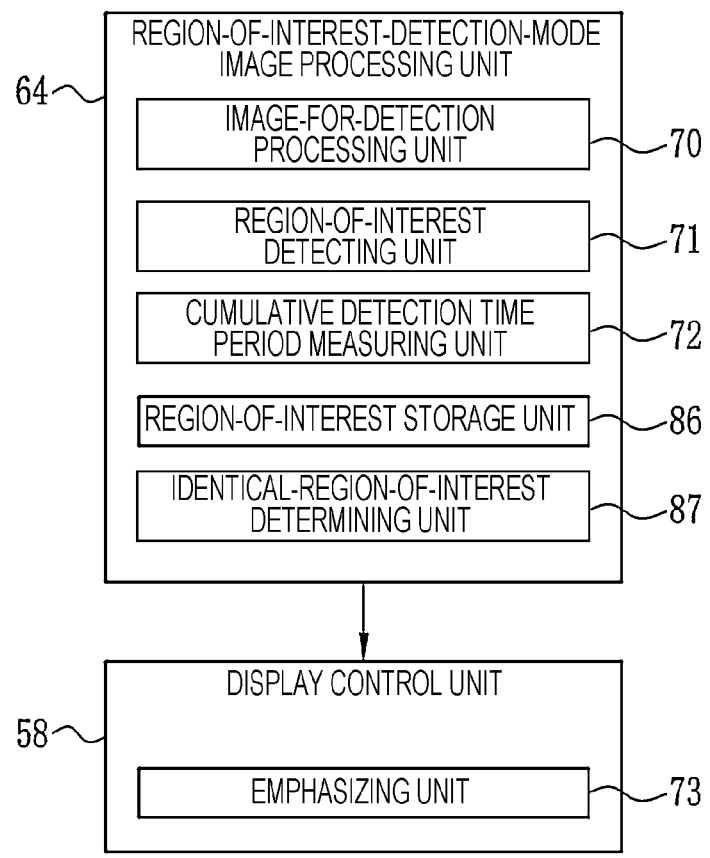
FIG. 11 is a block diagram illustrating functions of the region-of-interest-detection-mode image processing unit and the display control unit according to a third embodiment.

In this case, as illustrated in FIG. 11, the region-of-interest-detection-mode image processing unit 64 has a region-of-interest storage unit 86 and an identical-region-of-interest determining unit 87. The region-of-interest storage unit 86 stores the cumulative detection time periods of respective regions of interest previously detected by the region-of-interest detecting unit 71 and feature quantity information indicating the feature quantities of the respective regions of interest in association with each other. The region-of-interest storage unit 86 is constituted by a writable recording medium such as a random access memory (RAM), an electrically erasable programmable read-only memory (EEPROM), or a hard disk.

Figure 12:
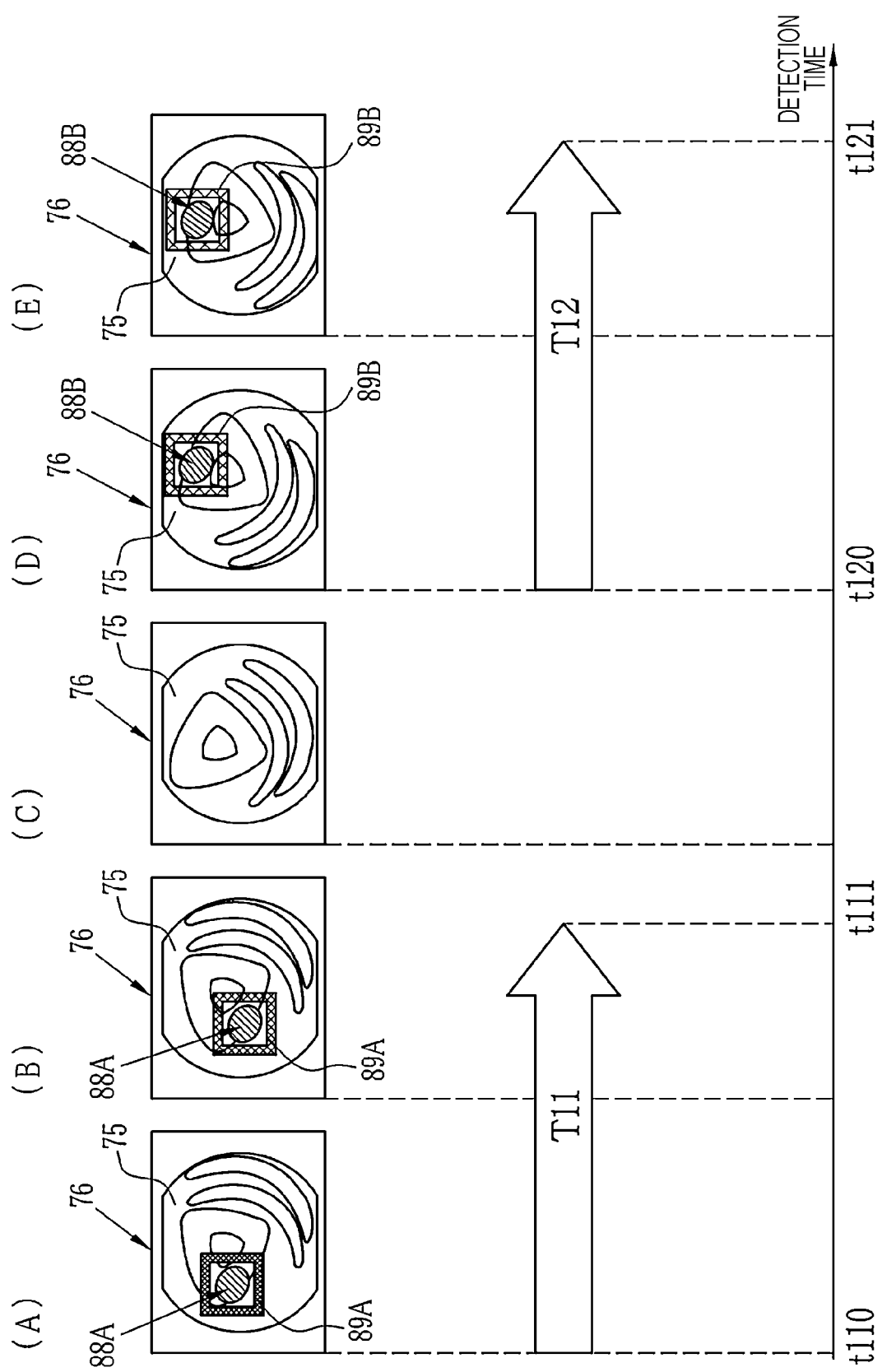
FIG. 12 is an explanatory diagram illustrating a relationship between a cumulative detection time period and emphasized display in a case where an identical-region-of-interest determining unit performs identical determination according to the third embodiment.

On the other hand, the identical-region-of-interest determining unit 87 determines, on the basis of the similarity between any one of the feature quantities of the regions of interest stored in the region-of-interest storage unit 86 and the feature quantity of a region of interest newly detected by the region-of-interest detecting unit 71, whether or not the newly detected region of interest is identical to any one of the previously detected regions of interest. FIG. 12 illustrates an example of a case where a lesion portion 88A as a previously detected region of interest and a lesion portion 88B as a newly detected region of interest are identical to each other. The endoscopic images illustrated in parts (A) to (E) of FIG. 12 are arranged in chronological order.

In this case, the lesion portion 88A is detected first as illustrated in parts (A) and (B) of FIG. 12, and is then not seen in the endoscopic image 75 as illustrated in part (C) of FIG. 12. In this example, the lesion portion 88A is a region of interest that is detected for the first time while endoscopic images are sequentially acquired, and identification determination is not performed unlike in a case where the lesion portion 88B is detected, which will be described below.

Time t110 at which the endoscopic image 75 illustrated in part (A) of FIG. 12 is acquired corresponds to the start of detection of the lesion portion 88A. At time t110, a cumulative detection time period T11 is 0, and the amount of emphasis of a FIG. 89A for emphasized display of the lesion portion 88A is maximum. At time t110, the cumulative detection time period measuring unit 72 starts measuring the cumulative detection time period T11.

As illustrated in parts (A) and (B) of FIG. 12, the amount of emphasis of the FIG. 89A gradually decreases as the cumulative detection time period T11 increases. At time t111, which is after the endoscopic image 75 illustrated in part (B) of FIG. 12 is acquired, the lesion portion 88A is not detected any longer. That is, at time t111, the measurement of the cumulative detection time period T11 is suspended, and the FIG. 89A for emphasized display is not displayed. In a case where the lesion portion 88A is not detected any longer, the region-of-interest-detection-mode image processing unit 64 stores the cumulative detection time period T11 of the lesion portion 88A measured by the cumulative detection time period measuring unit 72 and feature quantity information indicating the feature quantity of the lesion portion 88A in the region-of-interest storage unit 86 in association with each other. The feature quantity information is, for example, an image feature quantity such as pixel values of RGB image signals. The feature quantity information is not limited thereto and may be information indicating the position, size, shape, or the like of the region of interest.

After time t111, a state in which no region of interest is detected (the state illustrated in part (C) of FIG. 12) continues, and the lesion portion 88B is detected at time t120. That is, time t120 at which the endoscopic image 75 illustrated in part (D) of FIG. 12 is acquired corresponds to the start of detection of the lesion portion 88B. In such a case where the new lesion portion 88B is detected by the region-of-interest detecting unit 71, the identical-region-of-interest determining unit 87 determines, on the basis of the similarity between any one of the feature quantities of the regions of interest stored in the region-of-interest storage unit 86 and the feature quantity of the region of interest newly detected by the region-of-interest detecting unit 71, whether or not the newly detected region of interest is identical to any one of the previously detected regions of interest. That is, the identical-region-of-interest determining unit 87 determines that both the regions of interest are identical in a case where the similarity between the feature quantities of both the regions of interest is high (higher than or equal to a specific threshold value), and determines that both the regions of interest are not identical in a case where the similarity is low (lower than the specific threshold value).

In the example illustrated in parts (A) to (E) of FIG. 12, the similarity between the feature quantity of the lesion portion 88A stored in the region-of-interest storage unit 86 and the feature quantity of the lesion portion 88B newly detected by the region-of-interest detecting unit 71 is high, and thus the identical-region-of-interest determining unit 87 determines that the lesion portion 88A and the lesion portion 88B are identical to each other.

In a case where the newly detected lesion portion 88B is determined to be identical to the lesion portion 88A, which is any one of the previously detected regions of interest, the cumulative detection time period T11 of the previous lesion portion 88A that has been determined to be identical to the lesion portion 88B is taken over and measured. That is, the cumulative detection time period measuring unit 72 takes over the cumulative detection time period T11 and measures the cumulative detection time period from time t120 at which the endoscopic image 75 illustrated in part (D) of FIG. 12 is acquired and the lesion portion 88B is detected. Accordingly, the actual cumulative detection time period is equal to the sum of the cumulative detection time period T11 and a cumulative detection time period T12 from time t120.

At time t120, the cumulative detection time period measuring unit 72 takes over the cumulative detection time period T11 and restarts measurement. At time t120, the cumulative detection time period T12 is 0. Thus, as illustrated in part (D) of FIG. 12, a FIG. 89B for emphasized display of the lesion portion 88B at time t120 has the amount of emphasis corresponding to the cumulative detection time period T11 (=time t111−time t110) that has been taken over from the lesion portion 88A.

As illustrated in parts (D) and (E) of FIG. 12, the amount of emphasis of the FIG. 89B gradually decreases as the cumulative detection time period (T11+T12) increases. At time t121, which is after the endoscopic image 75 illustrated in part (E) of FIG. 12 is acquired, the lesion portion 88B is not seen in the endoscopic image 75. At time t121, the measurement of the cumulative detection time period (T11+T12) is suspended, and the FIG. 89B for emphasized display is not displayed. In a case where the lesion portion 88B is not detected any longer, the region-of-interest-detection-mode image processing unit 64 stores the cumulative detection time period (T11+T12) of the lesion portion 88B and feature quantity information indicating the feature quantity of the lesion portion 88B in the region-of-interest storage unit 86 in association with each other. In a case where a region of interest is newly detected after time t121, it is determined whether or not the newly detected region of interest is identical to a previously detected region of interest, similarly to the above.

On the other hand, in a case where the region of interest newly detected by the region-of-interest detecting unit 71 is determined not to be identical to any of the previously detected regions of interest, the cumulative detection time period measuring unit 72 resets the cumulative detection time period and starts measurement from the initial value (a counter value of 0).

As described above, as a result of taking over and measuring the cumulative detection time period of a previous region of interest that has been determined to be identical, emphasized display corresponding to the cumulative detection time period taken over from the previous region of interest is performed on a region of interest determined to be identical. Thus, a medical doctor is able to easily recognize that the region of interest identical to the previous region of interest is detected.

Fourth Embodiment

Figure 13:
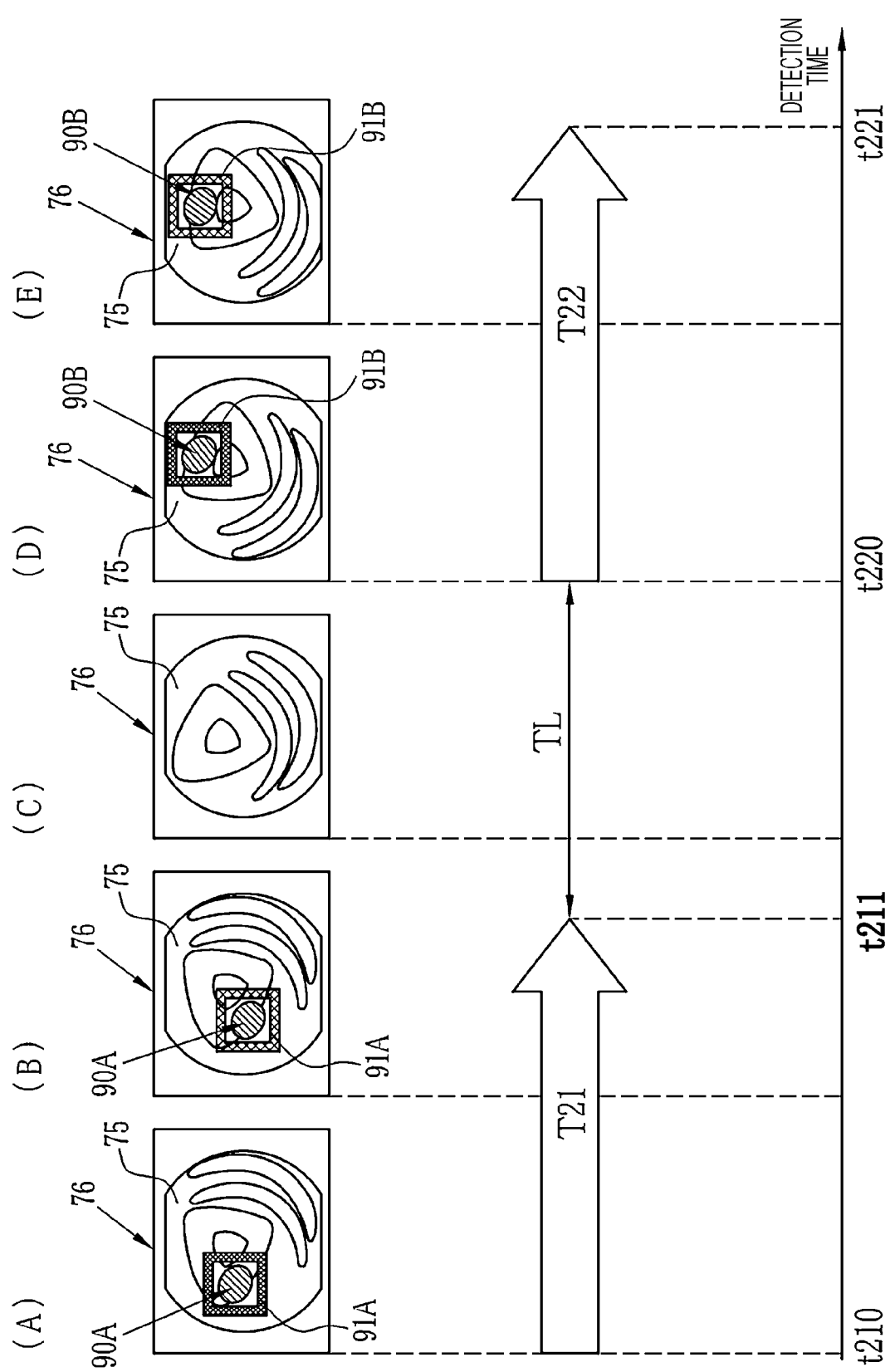
FIG. 13 is an explanatory diagram illustrating a relationship between a cumulative detection time period and emphasized display in a case where the identical-region-of-interest determining unit performs identical determination according to a fourth embodiment.

In the above-described third embodiment, in a case where a newly detected region of interest is determined to be identical to any one of previously detected regions of interest, the cumulative detection time period of the previous region of interest is taken over and measured. However, the cumulative detection time period is not necessarily taken over in every case where a newly detected region of interest is determined to be identical to a previously detected region of interest. Even in a case where a newly detected region of interest is determined to be identical to a previously detected region of interest, in a case where the time interval between the latest detection time of the previously detected region of interest and the detection time of the newly detected region of interest is greater than a predetermined value, the cumulative detection time period may be reset and then the measurement may be started. FIG. 13 illustrates an example of a case where a lesion portion 90A as a previously detected region of interest and a lesion portion 90B as a newly detected region of interest are identical to each other. The endoscopic images illustrated in parts (A) to (E) of FIG. 13 are arranged in chronological order.

In this case, the lesion portion 90A is detected first as illustrated in parts (A) and (B) of FIG. 13 and is then not seen in the endoscopic image 75 as illustrated in part (C) of FIG. 13. In this example, the lesion portion 90A is a region of interest that is detected for the first time while endoscopic images are sequentially acquired, and identification determination is not performed unlike in a case where the lesion portion 90B is detected, which will be described below.

Time t210 at which the endoscopic image 75 illustrated in part (A) of FIG. 13 is acquired corresponds to the start of detection of the lesion portion 90A. At time t210, a cumulative detection time period T21 is 0, and the amount of emphasis of a FIG. 91A for emphasized display of the lesion portion 90A is maximum. At time t210, the cumulative detection time period measuring unit 72 starts measuring the cumulative detection time period T21.

As illustrated in parts (A) and (B) of FIG. 13, the amount of emphasis of the FIG. 91A gradually decreases as the cumulative detection time period T21 increases. At time t211, which is after the endoscopic image 75 illustrated in part (B) of FIG. 13 is acquired, the lesion portion 90A is not detected any longer. That is, at time t211, the measurement of the cumulative detection time period T21 is suspended, and the FIG. 91A for emphasized display is not displayed. In a case where the lesion portion 90A is not detected any longer, the region-of-interest-detection-mode image processing unit 64 stores the cumulative detection time period T21 of the lesion portion 90A measured by the cumulative detection time period measuring unit 72, feature quantity information indicating the feature quantity of the lesion portion 90A, and the latest detection time t211 of the lesion portion 90A in the region-of-interest storage unit 86 in association with each other.

After time t211, a state in which no region of interest is detected (the state illustrated in part (C) of FIG. 13) continues, and the lesion portion 90B is detected at time t220. That is, time t220 at which the endoscopic image 75 illustrated in part (D) of FIG. 13 is acquired corresponds to the start of detection of the lesion portion 90B.

In such a case where the lesion portion 90B is newly detected by the region-of-interest detecting unit 71, the region-of-interest-detection-mode image processing unit 64 determines whether or not the lesion portion 90B is identical to any one of the previously detected regions of interest as in the above-described third embodiment, and also compares a time interval TL between the latest detection time t211 of the previously detected lesion portion 90A and the detection time t220 of the newly detected lesion portion 90B with a predetermined value. The predetermined value is set by assuming a case where a region of interest is present in the endoscopic image 75 but is unable to be detected for a functional reason of the apparatus, for example, the entire image is dark or focus is not achieved in the image sensor 38. Thus, the predetermined value to be compared with the above-described time interval TL is set by assuming a very short time period from when it becomes impossible to detect a region of interest for a functional reason of the apparatus to when a detectable state is restored.

Even in a case where the previously detected lesion portion 90A and the newly detected lesion portion 90B are determined to be identical to each other, in a case where the time interval TL between the detection time t211 and the detection time t220 is greater than the predetermined value, the cumulative detection time period measuring unit 72 resets the cumulative detection time period and starts measurement from the initial value (a counter value of 0). The cumulative detection time period measuring unit 72 starts measuring the cumulative detection time period T22 at time t220 at which the endoscopic image 75 illustrated in part (D) of FIG. 13 is acquired and the lesion portion 90B is detected.

As illustrated in part (D) of FIG. 13, at time t220, the cumulative detection time period T22 is 0, and the amount of emphasis of a FIG. 91B for emphasized display of the lesion portion 90B is maximum. As illustrated in parts (D) and (E) of FIG. 13, the amount of emphasis of the FIG. 91B gradually decreases as the cumulative detection time period T22 increases. At time t221, which is after the endoscopic image 75 illustrated in part (E) of FIG. 13 is acquired, the lesion portion 90B is not seen in the endoscopic image 75. At time t221, the measurement of the cumulative detection time period T22 is suspended, and the FIG. 91B for emphasized display is not displayed. In a case where the lesion portion 90B is not detected any longer, the region-of-interest-detection-mode image processing unit 64 stores the cumulative detection time period T22 of the lesion portion 90B measured by the cumulative detection time period measuring unit 72, feature quantity information indicating the feature quantity of the lesion portion 90B, and the latest detection time t221 of the lesion portion 90B in the regionof-interest storage unit 86 in association with each other. In a case where a region of interest is newly detected after time t221, it is determined whether or not the newly detected region of interest is identical to a previously detected region of interest, and the time interval between the detection times is compared with the predetermined value, similarly to the above.

On the other hand, in a case where the previously detected lesion portion 90A and the newly detected lesion portion 90B are determined to be identical to each other and the time interval TL between the latest detection time and the detection time of the new detection is smaller than or equal to the predetermined value, the cumulative detection time period T21 of the previous lesion portion 90A determined to be identical to the lesion portion 90B is taken over and measured, as in the above-described third embodiment.

In a case where the region of interest newly detected by the region-of-interest detecting unit 71 is determined not to be identical to any of the previously detected regions of interest, the cumulative detection time period is reset and measurement is started from the initial value (a counter value of 0) as in the above-described third embodiment.

In endoscopy, the insertion section 12a is inserted to a limit position in a lumen, and then a lesion portion is looked for while the insertion section 12a is slowly withdrawn from the lumen in a reverse direction along the same path as that at the time of insertion. Thus, a lesion detected during insertion may be detected again during withdrawal. In this embodiment, even in a case where a previously detected region of interest and a newly detected region of interest are determined to be identical to each other, in a case where the time interval TL between the latest detection time and the detection time of the new detection is greater than the predetermined value, the cumulative detection time period measuring unit 72 resets the cumulative detection time period and starts measurement from the initial value (a counter value of 0). There is a sufficient time interval between detection at the time of insertion and detection at the time of withdrawal. Thus, in such a case, it is possible to perform emphasized display to attract the attention of the operator during withdrawal. In a case where a lesion is detected again during withdrawal, the amount of emphasis is maximum and thus it is possible to prevent the medical doctor from overlooking the region of interest.

Fifth Embodiment

Figure 14:
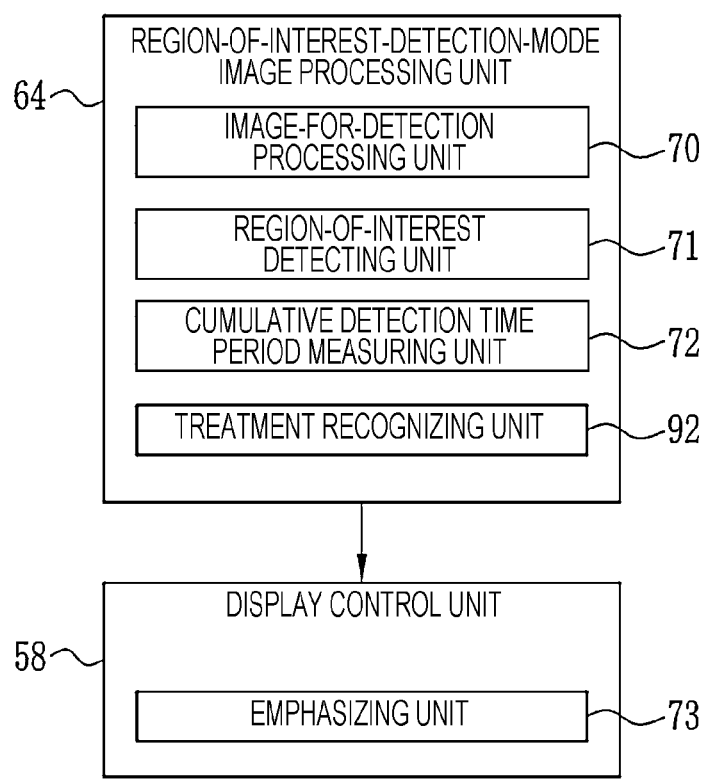
FIG. 14 is a block diagram illustrating functions of the region-of-interest-detection-mode image processing unit and the display control unit according to a fifth embodiment.

In the above-described fourth embodiment, even in a case where regions of interest are determined to be identical to each other, the cumulative detection time period is reset in a case where the time interval is greater than the predetermined value. Alternatively, in a case where it is recognized during imaging that a specific treatment has been performed, for example, air or liquid has been ejected or a treatment tool has been used, the cumulative detection time period may be reset. In this case, the region-of-interest-detection-mode image processing unit 64 includes a treatment recognizing unit 92, as illustrated in FIG. 14. The treatment recognizing unit 92 monitors ejection of air or liquid from the air/water supply nozzle as a specific treatment performed during imaging and recognizes, in response to receipt of a signal supplied when the air/water supply operation unit 13e is operated, that a specific treatment has been performed.

Figure 15:
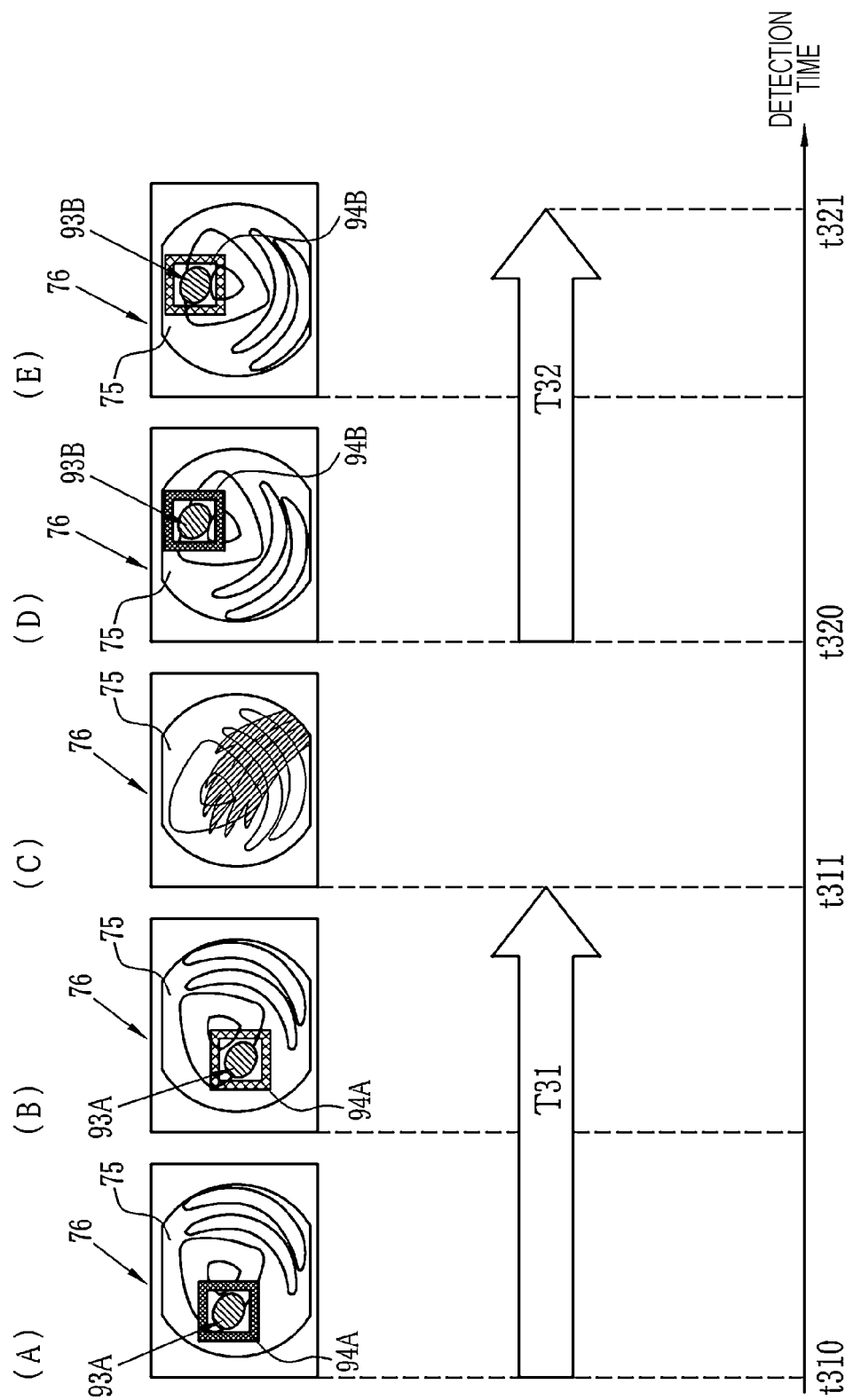
FIG. 15 is an explanatory diagram illustrating a relationship between a cumulative detection time period and emphasized display in a case where a treatment recognizing unit performs treatment recognition according to the fifth embodiment.

FIG. 15 illustrates an example of a case where a lesion portion 93A as a previously detected region of interest and a lesion portion 93B as a newly detected region of interest are identical to each other. The endoscopic images illustrated in parts (A) to (E) of FIG. 15 are arranged in chronological order.

In this case, the lesion portion 93A is detected first as illustrated in parts (A) and (B) of FIG. 15, and then ejection of air or liquid as a specific treatment is performed in an observation target as illustrated in part (C) of FIG. 15.

Time t311 at which the endoscopic image 75 illustrated in part (C) of FIG. 15 is acquired is the time at which the treatment recognizing unit 92 recognizes that ejection of air or liquid as a specific treatment has been performed. In response to the recognition of the specific treatment by the treatment recognizing unit 92, the cumulative detection time period measuring unit 72 stops measuring a cumulative detection time period T31 and resets the cumulative detection time period. Thus, a FIG. 94A for emphasized display is not displayed. After time t311, a state in which the specific treatment is being performed (the state illustrated in part (C) of FIG. 15) continues until immediately before time t320. In this embodiment, as in the third and fourth embodiments, whether or not regions of interest are identical to each other may be determined. In a case where the regions of interest are determined to be identical to each other, the cumulative detection time period may be taken over and measured under a certain condition. However, in a case where a specific treatment is recognized, the cumulative detection time period is preferentially reset regardless of whether the regions of interest are identical to each other.

At time t320, the lesion portion 93B is detected. That is, time t320 at which the endoscopic image 75 illustrated in part (D) of FIG. 15 is acquired corresponds to the start of detection of the lesion portion 93B. As illustrated in part (D) of FIG. 15, at time t320, a cumulative detection time period T32 is 0, and the amount of emphasis of a FIG. 94B for emphasized display of the lesion portion 93B is maximum. As illustrated in parts (D) and (E) of FIG. 15, the amount of emphasis of the FIG. 94B gradually decreases as the cumulative detection time period T32 increases. At time t321, which is after the endoscopic image 75 illustrated in part (E) of FIG. 15 is acquired, the lesion portion 93B is not seen in the endoscopic image 75.

In a case where ejection of air or liquid is performed as a specific treatment during endoscopy, an endoscopic image significantly changes. Specifically, an ejected liquid is depicted in the endoscopic image or the observation target is deformed by ejection of air. Thus, in a case where a specific treatment is performed, a medical doctor may lose sight of a region of interest even if he/she has recognized the region of interest before the specific treatment. In this embodiment, in a case where a specific treatment is performed, the cumulative detection time period measuring unit 72 resets the cumulative detection time period and starts measurement from the initial value (a counter value of 0). In a case where a region of interest is detected again after the specific treatment, the amount of emphasis is maximum and thus it is possible to prevent the medical doctor from overlooking the region of interest.

In this embodiment, ejection of air or liquid is described as an example of a specific treatment, but the specific treatment is not limited thereto. Any specific treatment having an influence on an endoscopic image may be applied, for example, treatment with a treatment tool. In this embodiment, as a method for recognizing a specific treatment, a signal of an operation unit is received and recognized, but the method is not limited thereto. A specific treatment may be recognized by determining ejection of air or liquid or the shape of a treatment tool by analyzing an endoscopic image.

In each of the above-described embodiments, the display control unit 58 changes the transparency of a figure for emphasized display in the case of changing the emphasized display in accordance with a cumulative detection time period, but change of emphasized display is not limited thereto. The color of a figure for emphasized display may be changed from a specific color to another color, for example, from green to red.

Figure 16:
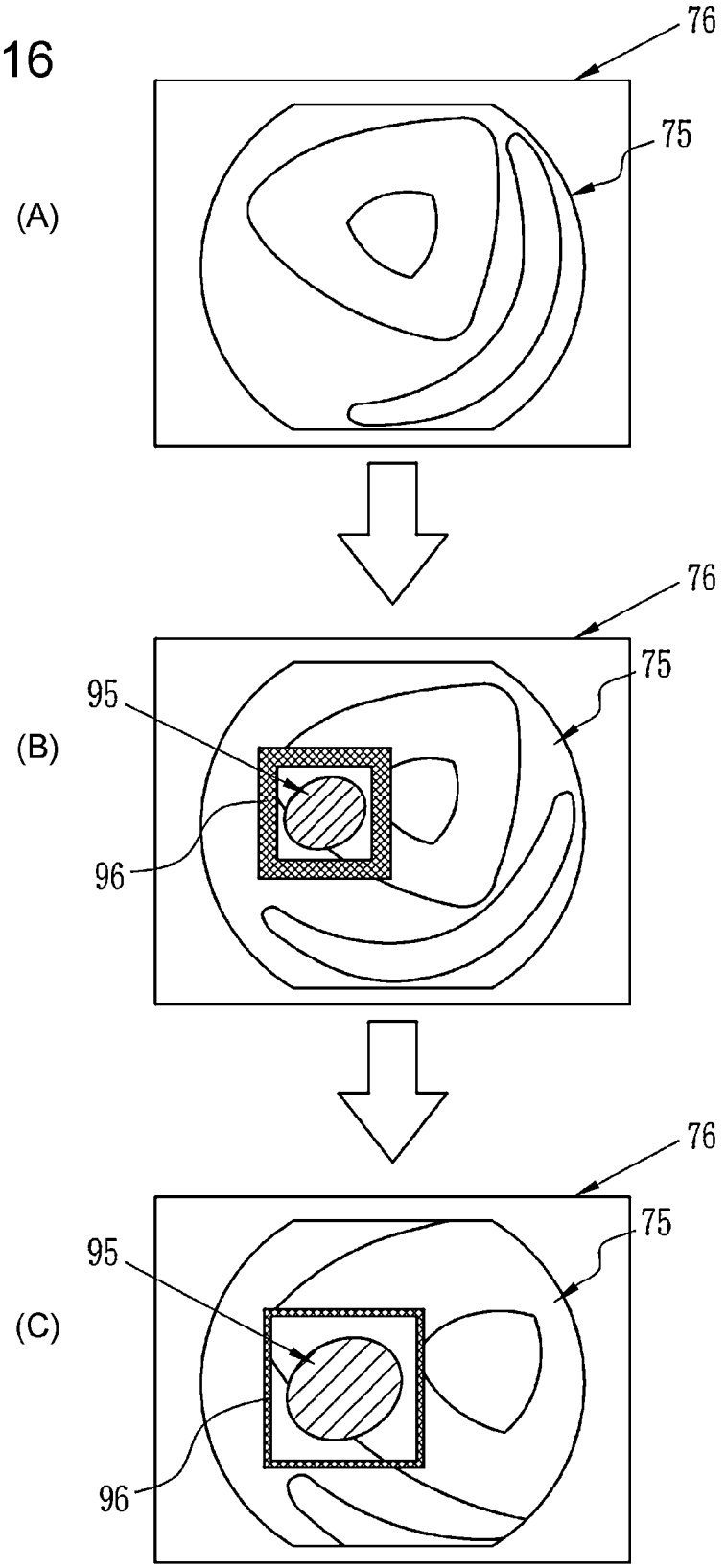
FIG. 16 is an explanatory diagram illustrating a first modification example of the case of performing emphasized display of a region of interest.

In the case of changing emphasized display in accordance with a cumulative detection time period, the shape of a figure may be changed instead of the transparency or color of the figure. As illustrated in FIG. 16, a frame-shaped figure surrounding a region of interest may be displayed for emphasized display, and the thickness of the frame-shaped figure may be changed in accordance with a cumulative detection time period.

In this case, in a case where a lesion portion 95 as a region of interest is detected in a state in which no region of interest is detected (part (A) of FIG. 16), the display control unit 58 causes a frame-shaped FIG. 96 surrounding the lesion portion 95 to be displayed for emphasized display, and changes the emphasized display in accordance with the cumulative detection time period measured by the cumulative detection time period measuring unit 72. Specifically, as illustrated in part (B) of FIG. 16, the display control unit 58 maximizes the amount of emphasis of the FIG. 96, that is, maximizes the thickness of the frame of the FIG. 96, at the start of detection of the lesion portion 95 as a region of interest. In this case, the cumulative detection time period measured by the cumulative detection time period measuring unit 72 is 0. Subsequently, as illustrated in part (C) of FIG. 16, the display control unit 58 gradually decreases the amount of emphasis of the FIG. 96, that is, gradually decreases the thickness of the frame of the FIG. 96, as the cumulative detection time period increases.

In each of the above-described embodiments, the figure for emphasized display is rectangular frame shaped, but the shape is not limited thereto. Any frame shape other than a rectangle (square) capable of surrounding a region of interest, for example, polygon, circle, or oval, may be used.

In each of the above-described embodiments, the display control unit 58 superimposes a frame-shaped figure on a position of a region of interest for emphasized display, but the emphasized display is not limited thereto. For emphasized display, the color of a region of interest may be changed, and the color may be gradually returned to the color before change in accordance with a cumulative detection time period.

Figure 17:
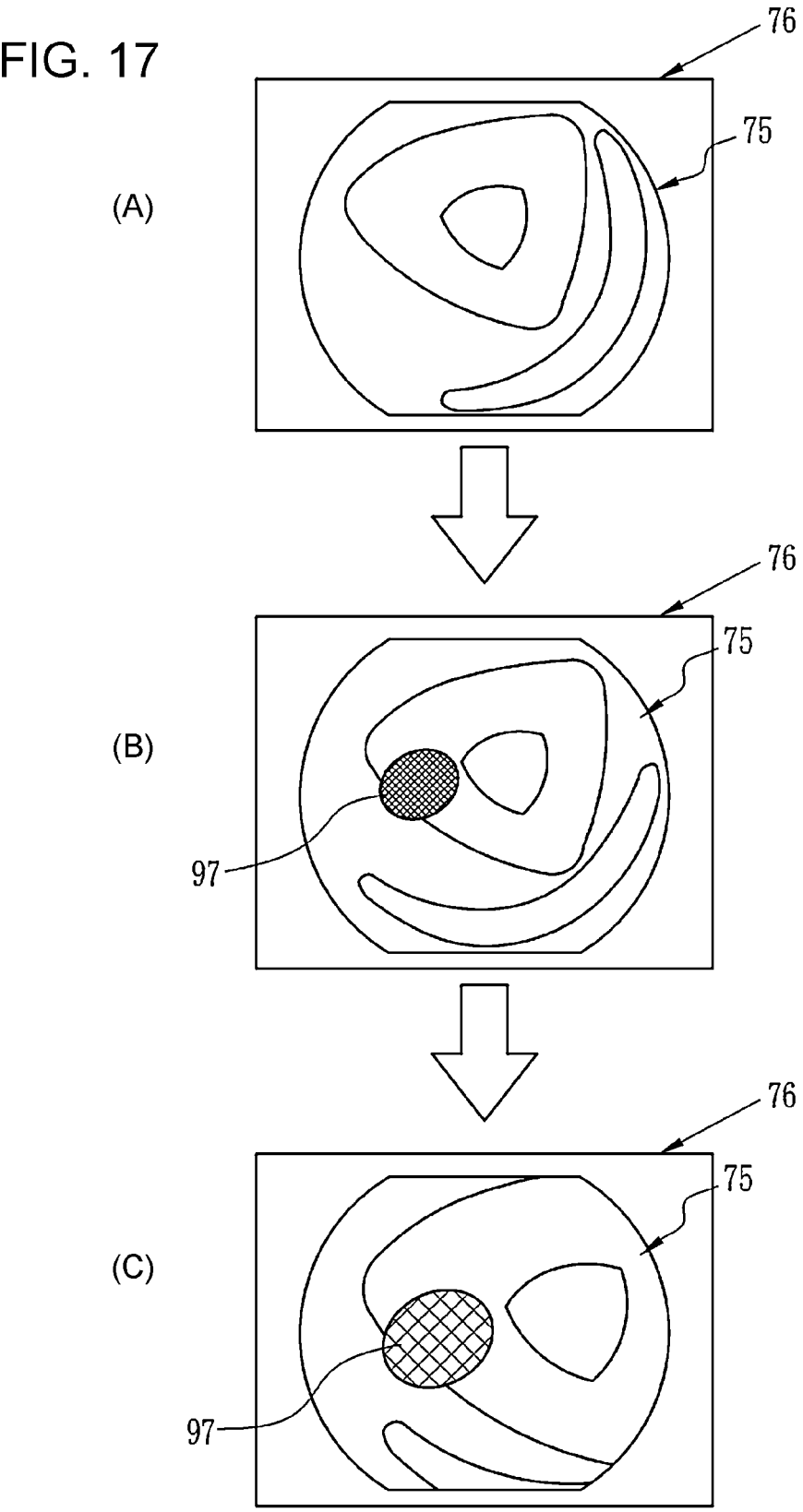
FIG. 17 is an explanatory diagram illustrating a second modification example of the case of performing emphasized display of a region of interest.

In this case, in a case where a lesion portion 97 as a region of interest is detected in a state in which no region of interest is detected (part (A) of FIG. 17), the display control unit 58 causes the lesion portion 97 to be displayed in a color different from the original color for emphasized display, for example, by extracting a color contained in high proportion in the lesion portion 97 and replacing the color with a color having a different hue, and changes the emphasized display in accordance with the cumulative detection time period measured by the cumulative detection time period measuring unit 72. Specifically, as illustrated in part (B) of FIG. 17, in a case where a red portion is contained in high proportion in the lesion portion 97 at the start of detection of the lesion portion 97 as a region of interest, the display control unit 58 causes the lesion portion 97 to be displayed with the red portion being replaced with a green portion having an entirely different hue. Such a state in which the color of the lesion portion 97 has been replaced with a color having an entirely different hue is referred to as a state in which the amount of emphasis is maximum. In this case, the cumulative detection time period measured by the cumulative detection time period measuring unit 72 is 0.

Subsequently, as illustrated in part (C) of FIG. 17, the display control unit 58 gradually decreases the amount of emphasis of the lesion portion 97, that is, gradually returns the color of the color-replaced portion of the lesion portion 97 from green to red, a color before change, as the cumulative detection time period increases. In parts (B) and (C) of FIG. 17, the difference from the color before change of the lesion portion 97 is expressed by the density of hatching applied to the lesion portion 97 for convenience of illustration. The hatching density is higher in the lesion portion 97 in part (B) of FIG. 17 than in the lesion portion 97 in part (C) of FIG. 17.

In the example illustrated in FIG. 17, only the portion of the lesion portion 97 as a region of interest is displayed in an emphasized manner by changing the color thereof, but the emphasized display is not limited thereto. A range slightly larger than the lesion portion 97 may be displayed in an emphasized manner by changing the color thereof. The emphasized display of the lesion portion 97 is not limited thereto. Any image processing may be applied as long as visual distinction from the surroundings is possible, such as hue change processing, chroma change processing, contrast processing, negative-positive reverse processing, or filtering processing. Alternatively, emphasized display using pixel values of the lesion portion 97 and emphasized display using a figure surrounding a lesion portion in each of the above-described embodiments may be combined.

Although an observation target is illuminated by using the four-color LEDs 20a to 20d in each of the above-described embodiments, the observation target may be illuminated by using a laser light source and a fluorescent body. Although an observation target is illuminated by using the four-color LEDs 20a to 20d in each of the above-described embodiments, the observation target may be illuminated by using a white light source such as a xenon lamp and a rotary filter. Imaging of an observation target may be performed by using a monochrome image sensor instead of the color image sensor 38.

In the above-described embodiments, the medical image processing apparatus of the present invention is applied to an endoscope system that acquires an endoscopic image as a medical image. Obviously, the medical image processing apparatus of the present invention can be applied to various types of endoscope systems, such as a capsule endoscope. Also, the medical image processing apparatus of the present invention can be applied to various types of medical image apparatuses that acquire other types of medical images, such as an X-ray image, a CT image, an MR image, an ultrasound image, a pathological image, and a positron emission tomography (PET) image.

In the above-described embodiments, the hardware structure of a processing unit that executes various processing operations, such as the image processing unit 56, may be various types of processors described below. The various types of processors include a central processing unit (CPU), which is a general-purpose processor executing software (program) and functioning as various processing units; a graphical processing unit (GPU); a programmable logic device (PLD), which is a processor whose circuit configuration is changeable after manufacturing, such as a field programmable gate array (FPGA); a dedicated electric circuit, which is a processor having a circuit configuration designed exclusively for executing various processing operations, and the like.

A single processing unit may be constituted by one of these various types of processors or may be constituted by a combination of two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of these various types of processors is, more specifically, electric circuitry including a combination of circuit elements, such as semiconductor elements.

REFERENCE SIGNS LIST 10 endoscope system
12 endoscope
12a insertion section
12b operation section
12c bending portion
12d distal end portion
13a angle knob
13b still image acquiring unit
13c mode switching unit
13d zoom operation unit
14 light source device
16 processor device
18 monitor
19 console
20 light source unit
20a V-LED
20b B-LED
20c G-LED
20d R-LED
22 light source control unit
23 wavelength cut filter
24 light guide
30a illumination optical system
30b imaging optical system
32 illumination lens
34 objective lens
36 magnifying optical system
36a zoom lens
36b lens driving unit
38 image sensor
40 CDS circuit
42 AGC circuit
44 A/D conversion circuit
50 image signal acquiring unit
52 DSP
54 noise reducing unit
56 image processing unit
58 display control unit
60 normal-mode image processing unit
62 special-mode image processing unit
64 region-of-interest-detection-mode image processing unit
70 image-for-detection processing unit
71 region-of-interest detecting unit
72 cumulative detection time period measuring unit
73 emphasizing unit
75 endoscopic image
76 display screen
77 figure
78 lesion portion
81 first lesion portion
82 second lesion portion
83 figure
84 figure
86 region-of-interest storage unit
87 identical-region-of-interest determining unit
88A lesion portion
88B lesion portion
89A FIG.
89B FIG.
90A lesion portion
90B lesion portion
91A FIG.
91B figure
treatment recognizing unit
93A lesion portion
93B lesion portion
94A FIG.
94B figure
95 lesion portion
96 figure
97 lesion portion

What is claimed is:

1. A medical image processing apparatus comprising:
one or more hardware processors configured to:
acquire a medical image, the medical image being obtained through imaging of an observation target performed by an imaging device;
detect a region of interest in the observation target from the medical image;
measure a first cumulative detection time period during which the region of interest remains detected;
cause the region of interest detected from the medical image to be displayed in a manner of emphasized display and that changes the emphasized display in accordance with the first cumulative detection time period;
superimpose, for the emphasized display, a figure on a position of the region of interest in the medical image;
determine whether a newly detected region of interest is identical to any one of the previously detected regions of interest during imaging performed by the imaging device; and
take over the first cumulative detection time period and measure a second cumulative detection time period of the previous region of interest that has been determined to be identical to the newly detected region of interest so as to change the emphasized display in accordance with the second cumulative detection time period.

2. The medical image processing apparatus according to claim 1, wherein the one or more hardware processors is configured to maximize an amount of emphasis of the emphasized display at a start of detection of the region of interest and gradually decrease the amount of emphasis of the emphasized display as the second cumulative detection time period increases.

3. The medical image processing apparatus according to claim 1, wherein in a case where the one or more hardware processors is to have detected a plurality of regions of interest during imaging performed by the imaging device, the one or more hardware processors is further configured to measure cumulative detection time periods of the respective regions of interest that have been detected, and The one or more hardware processors is further configured to change each emphasized display in accordance with the cumulative detection time periods of the respective regions of interest.

4. The medical image processing apparatus according to claim 1, wherein the one or more hardware processors is further configured to store cumulative detection time periods of respective regions of interest previously detected by the one or more hardware processors and feature quantity information indicating feature quantities of the respective regions of interest in association with each other; and in a case where the one or more hardware processors determines that the newly detected region of interest is not identical to any of the previously detected regions of interest, the one or more hardware processors is configured to reset and start measuring a cumulative detection time period of the region of interest newly detected by the one or more hardware processors.

5. The medical image processing apparatus according to claim 4, wherein the one or more hardware processors is configured to store latest detection times of the respective previously detected regions of interest in association with the cumulative detection time periods and the feature quantity information, and in a case where the one or more hardware processors is to have determined that the newly detected region of interest is identical to any one of the previously detected regions of interest during imaging performed by the imaging device and a time interval between the latest detection time of the previously detected region of interest that has been determined to be identical to the newly detected region of interest and a detection time of the newly detected region of interest is greater than a predetermined value, the one or more hardware processors is configured to reset and start measuring another cumulative detection time period of the region of interest newly detected by the one or more hardware processors.

6. The medical image processing apparatus according to claim 1, wherein the one or more hardware processors is further configured to recognize that a specific treatment has been performed in the observation target, and in a case where the one or more hardware processor is to have recognized that the specific treatment has been performed during imaging performed by the imaging device, the one or more hardware processor is further configured to reset and restart measuring another cumulative detection time period of a region of interest newly detected by the one or more hardware processor.

7. The medical image processing apparatus according to claim 1, wherein the one or more hardware processor is further configured to superimpose, for the emphasized display, a figure on a position of the region of interest in the medical image.

8. The medical image processing apparatus according to claim 7, wherein the one or more hardware processor is further configured to change, in accordance with the second cumulative detection time period, a color of the figure to be displayed for the emphasized display.

9. The medical image processing apparatus according to claim 7, wherein the one or more hardware processor is further configured to change, in accordance with the second cumulative detection time period, a transparency of the figure to be superimposed on the region of interest.

10. The medical image processing apparatus according to claim 7, wherein the one or more hardware processor is further configured to change, in accordance with the second cumulative detection time period, a shape of the figure to be displayed for the emphasized display.

11. The medical image processing apparatus according to claim 10, wherein the one or more hardware processor is further configured to cause a frame-shaped figure surrounding the region of interest to be displayed for the emphasized display and changes a thickness of a frame of the figure in accordance with the second cumulative detection time period.

12. The medical image processing apparatus according to claim 1, wherein the one or more hardware processor is further configured to perform the emphasized display by changing a color of the region of interest and returns the color of the region of interest to a color before change in accordance with the second cumulative detection time period.

13. The medical image processing apparatus according to claim 1, wherein the one or more processors are further configured to reset and start measuring another cumulative detection time period of the newly detected region of interest, in a case where a time interval between the latest detection time of the previously detected region of interest that has been determined to be identical to the newly detected region of interest and a detection time of the newly detected region of interest is greater than a predetermined value.

14. The medical image processing apparatus according to claim 1, wherein the one or more processors are further configured to:

store feature quantities of respective previously detected regions of interest; and determine whether or not a newly detected region of interest is identical to any one of the previously detected regions of interest, based on a similarity between any one of the stored feature quantities of the respective previously detected regions of interest and a feature quantity of the newly detected region of interest.

15. The medical image processing apparatus according to claim 1, wherein the one or more processors are further configured to increase an amount of transparency of the figure as the second cumulative detection time period increases.

16. The medical image processing apparatus according to claim 1, wherein the figure has a frame-shape, and the one or more processors are further configured to decrease a thickness of a frame of the figure as the second cumulative detection time period increases.

17. An endoscope system comprising:

a light source device that emits illumination light for illuminating an observation target;

an endoscope having an imaging device that performs imaging of the observation target illuminated with the illumination light;
one or more hardware processors configured to:
acquire a medical image, the medical image being obtained through imaging of the observation target performed by the imaging device;
detect a region of interest in the observation target from the medical image acquired by the one or more hardware processors;
measure a first cumulative detection time period during which the region of interest remains detected; and
cause the region of interest detected from the medical image by the one or more hardware processors to be displayed in a manner of emphasized display and that changes the emphasized display in accordance with the first cumulative detection time period;
superimpose, for the emphasized display, a figure on a position of the region of interest in the medical image;
determine whether a newly detected region of interest is identical to any one of the previously detected regions of interest during imaging performed by the imaging device; and
take over the first cumulative detection time period and measure a second cumulative detection time period of the previous region of interest that has been determined to be identical to the newly detected region of interest so as to change the emphasized display in accordance with the second cumulative detection time period; and
a display device that displays the medical image to which the emphasized display is applied.

18. A method for operating a medical image processing apparatus, comprising following steps performed by a processor:
acquiring a medical image, the medical image being obtained through imaging of an observation target performed by an imaging device;
detecting a region of interest in the observation target from the acquired medical image;
measuring a first cumulative detection time period during which the region of interest remains detected; and
causing the region of interest detected from the medical image to be displayed in a manner of emphasized display and changing the emphasized display in accordance with the first cumulative detection time period;
superimposing, for the emphasized display, a figure on a position of the region of interest in the medical image;
determining whether a newly detected region of interest is identical to any one of the previously detected regions of interest during imaging performed by the imaging device; and
taking over the first cumulative detection time period and measuring a second cumulative detection time period of the previous region of interest that has been determined to be identical to the newly detected region of interest so as to change the emphasized display in accordance with the second cumulative detection time period.

* * * * *